United States Patent [19]

Saji et al.

[11] Patent Number: 5,532,372

[45] Date of Patent: Jul. 2, 1996

[54] IMIDE DERIVATIVES, AND THEIR PRODUCTION AND USE

[75] Inventors: Ikutaro Saji; Masayuki Muto; Norihiko Tanno; Mayumi Yoshigi, all of Osaka, Japan

[73] Assignee: Sumitomo Pharmaceuticals Company, Ltd., Osaka, Japan

[21] Appl. No.: 113,320

[22] Filed: Aug. 30, 1993

Related U.S. Application Data

[63] Continuation of Ser. No. 726,172, Jul. 5, 1991, abandoned.

[30] Foreign Application Priority Data

Jul. 6, 1990 [JP] Japan ................... 2-180271

[51] Int. Cl.$^6$ ............... C07D 417/14; A61K 31/495
[52] U.S. Cl. .................. 544/368; 546/17; 546/16; 546/199; 546/200; 546/198; 546/201; 546/225; 546/243; 544/230; 544/231; 514/255; 514/321
[58] Field of Search ............................. 544/368

[56] References Cited

U.S. PATENT DOCUMENTS

| | | | |
|---|---|---|---|
| 4,411,901 | 10/1983 | Temple, Jr. et al. | 544/368 |
| 4,590,196 | 5/1986 | Smith et al. | 544/368 |
| 4,656,173 | 4/1987 | Yevich et al. | 514/253 |
| 4,745,117 | 5/1988 | Ishizumi et al. | 544/368 |
| 4,812,461 | 3/1989 | Antoku et al. | 546/198 |
| 4,843,078 | 6/1989 | Ishizumi et al. | 544/295 |
| 4,937,249 | 6/1990 | Antoku et al. | 546/187 |

FOREIGN PATENT DOCUMENTS

| | | | |
|---|---|---|---|
| 0009465 | 4/1980 | European Pat. Off. | 544/291 |
| 0080104 | 6/1983 | European Pat. Off. | 546/198 |
| 0109562 | 6/1983 | European Pat. Off. | 546/198 |
| 0082402 | 4/1986 | European Pat. Off. | 544/373 |
| 0196096 | 10/1986 | European Pat. Off. | 544/362 |
| 0261688 | 3/1988 | European Pat. Off. | 546/198 |
| 0314098 | 5/1989 | European Pat. Off. | 546/198 |
| 3422411 | 1/1985 | Germany | 546/16 |
| 1570374 | 7/1980 | United Kingdom | 546/199 |

OTHER PUBLICATIONS

Seeman "Dopamine Receptors and the Dopamamine hypothesis of Schizophrenia" (Synapse) vol. 1, pp. 133–152 (1987).
Seeman "Brain Dopamine Receptors" (Pharmaeological Reviews) vol. 32, No. 3, pp. 230–231 (1981).
Ban "Psycopharacologlogly for the Agerl" pp. 42–73 (Karger) (1980).
Dunner et al. "Psychopharmacology: The Third Generation of Progress" (Raven) (1987) pp. 1097–1083.
Chemical Abstracts 78:58177q (1973).
The Merck Index, 11, 229 (1989) No. 1493.
The Merck Index, 11, 689 (1989) No. 4297.
Chou "Drug Treatment of Acute Mania" (Drugs of Today) vol 28, No. 2 pp.119–130 (1992).
Barnett "Pharmacological Evaluation of Antianxiety Agents in Laboratory Animals" (Antianxiety Agents) pp. 28–79 (witey) (1986).
Vogel et al. "A Simple and Reliable Conflict Procedere for testing Anti–Anxiety Agents" (Psychopharmacologia) (Berlin) vol 21, pp. 1–7 (1971).

*Primary Examiner*—Robert T. Bond
*Attorney, Agent, or Firm*—Birch, Stewart, Kolasch & Birch

[57] ABSTRACT

An imide compound of the formula:

$$Z-D-N\underset{\diagdown\_\diagup}{\overset{\diagup\overline{\phantom{xx}}\diagdown}{\phantom{N}}}G-Ar \quad (I)$$

wherein

Z is a group of the formula:

$$R^1\diagdown\underset{R^2\diagup}{\overset{(CH_2)_n}{\phantom{X}}}\underset{R^3\ R^4}{\overset{\phantom{X}}{\diagup\phantom{X}\diagdown}}\overset{O}{\underset{B}{\phantom{X}}}\diagdown N-$$

in which the substituents are defined herein, and n is an integer of 0 to 1;

D is a group of the formula:

$$-(CH_2)_p-A-(CH_2)_q-$$

in which A is a non-aromatic hydrocarbon ring optionally bridged with a lower alkylene group or an oxygen atom, said non-aromatic hydrocarbon ring and said lower alkylene group being each optionally substituted with at least one lower alkyl, and p and q are each an integer of 0, 1 or 2; and Ar is an aromatic group, a heterocyclic aromatic group, a benzoyl group, a phenoxy group or a phenylthio group and G is >N—, >CH— or >COH— or Ar is a biphenylmethylidene group and G is >C=, all of the above groups being each optionally substituted with at least one of lower alkyl, lower alkoxy and halogen; and its acid addition salts, useful as an antipsycotic agent.

20 Claims, No Drawings

IMIDE DERIVATIVES, AND THEIR PRODUCTION AND USE

This application is a continuation, of application Ser. No. 07/726,172 filed on Jul. 5, 1991, now abandoned.

The present invention relates to imide derivatives, and their production and use. More particularly, it relates to novel imide compounds and their acid addition salts, and their production processes and their use as anti-psycotic agents (neuroleptic agents, anti-anxiety agents), especially for therapy of schizophrenia, senile insanity, manic-depressive psychosis, neurosis, etc.

There are known some imide compounds having an anti-psycotic activity, of which typical examples are as follows:

Conventional antipsychotic agents are generally accompanied by a central or peripheral system side effect such as extrapyramidal motor disturbance (e.g. Parkinsonism) and depression of blood pressure (e.g. orthostatic hypotension) and produce a great problem on clinic (e.g. L. S. Goodman et al.: The Pharmacological Basis of Therapeutics, New York, p. 387 (1985); Gendai Iryo (Modern Medical Therapy), 22, p. 22 (1990)).

The problem underlying the present invention is to provide an excellent psychotic agent suppressed in the above side effect as generally observed on the conventional antipsychotic agents. An extensive study has been made. As the result, it has been found that imide compounds wherein the imide portion and the piperazine or piperidine ring are bonded with intervention of an alkylene chain comprising a

| Structure | Remarks |
|---|---|
| [structure] | Tiaspirone; JP-A-61-251683, JP-A-58-110576 |
| [structure] | Buspirone; The Merck Index, 11, 229 (1989) |
| [structure] | Gepirone The Merck Index, 11, 689 (1989) |
| [structure] | JP-B-01-28756 |
| [structure] | US-A-4,745,117 |
| [structure] | JP-A-01-199967 |

These conventional imide compounds are characteristic in that the imide portion and the piperazine or piperidine ring are bonded together with intervention of a straight alkylene chain.

non-aromatic hydrocarbon ring therein show the desired pharmacological action. Any imide compound wherein the alkylene chain present between the imide portion and the piperazine or piperidine ring comprises a non-aromatic hydrocarbon ring has never been known. The present invention is based on the above findings.

Accordingly, an object of the present invention is to provide an imide compound of the formula:

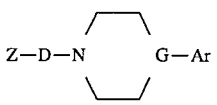   (I)

wherein
Z is a group of the formula:

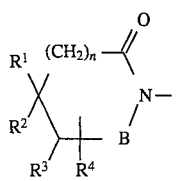

in which B is a carbonyl group or a sulfonyl group $R^1$, $R^2$, $R^3$ and $R^4$ are each a hydrogen atom or a lower alkyl group, or $R^1$ and $R^2$ or $R^1$ and $R^3$ may be combined together to make a non-aromatic hydrocarbon ring or $R^1$ and $R^3$ may be combined together to make an aromatic ring, said non-aromatic hydrocarbon ring being optionally bridged with a lower alkylene group or an oxygen atom therein and said aromatic hydrocarbon ring, said non-aromatic hydrocarbon ring and said lower alkylene group being each optionally substituted with at least one lower alkyl, and n is an integer of 0 or 1;

D is a group of the formula:

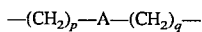

in which A is a non-aromatic hydrocarbon ring optionally bridged with a lower alkylene group or an oxygen atom, said non-aromatic hydrocarbon ring and said lower alkylene group being each optionally substituted with at least one lower alkyl, and p and q are each an integer of 0, 1 or 2; and Ar is an aromatic group, a heterocyclic aromatic group, a benzoyl group, a phenoxy group or a phenylthio group and G is >N—, >CH— or >COH— or Ar is a biphenylmethylidene group and G is >C=, all of the above groups being each optionally substituted with at least one of lower alkyl, lower alkoxy and halogen; and its acid addition salts.

In the above significances, the term "lower" is intended to mean generally a group having not more than 8 carbon atoms, particularly not more than 5 carbon atoms, unless otherwise specified. The term "lower alkyl" includes an alkyl group preferably having not more than 4 carbon atoms (e.g. methyl, ethyl, propyl, 2-propyl, butyl). The term "lower alkoxy" covers an alkoxy group preferably having not more than 4 carbon atoms (e.g. methoxy, ethoxy, propoxy, 2-propoxy, butoxy). The term "lower alkylene" covers an alkylene group preferably having not more than 3 carbon atoms (e.g. methylene, ethylene, trimethylene). The term "halogen" includes chlorine, bromine, iodine and fluorine.

The non-aromatic hydrocarbon ring includes particularly the one having not more than 7 carbon atoms such as a cycloalkane ring having not more than 7 carbon atoms or a cycloalkene ring having not more than 7 carbon atoms. Examples of the cycloalkane ring include cyclopropane, cyclobutane, cyclopentane, cyclohexane and cycloheptane. Examples of the cycloalkene ring are cyclopentene, cyclohexene, cycloheptene, etc.

The non-aromatic hydrocarbon ring bridged with a lower alkylene group or an oxygen atom may be, for instance, the one having not more than 10 ring carbon atoms and includes specifically bicyclo[1.1.1]pentane, bicyclo[-2.1.1]hexane, bicyclo[2.1.1]hex-2-ene, bicyclo[2.2.1]heptane, bicyclo [2.2.1]hept-2-ene, bicyclo[2.2.2]octane, bicyclo[2.2.2]oct-2-ene, bicyclo[4.1.1]octane, bicyclo[-4.1.1]oct-2-ene, bicyclo[4.1.1]oct-3-ene, bicyclo[3.2.1]octane, bicyclo [3.2.1]oct-2-ene, bicyclo[3.2.1]oct-3-ene, bicyclo[3.2.1]oct-6-ene, bicyclo[3.2.2]nonane, bicyclo[3.2.2]non-2-ene, bicyclo[3.2.2]non-3-ene, bicyclo[3.2.2]-non-6-ene, 2-oxabicyclo[1.1.1]butane, 2-oxabicyclo[2.1.1]pentane, 2-oxabicyclo[2.1.1]pent-4-ene, 7-oxabicyclo[2.2.1]hexane, 7-oxabicyclo[2.2.1]hex-2-ene, 7-oxabicyclo[4.1.1]heptane, 7-oxabicyclo[4.1.1]hept-2-ene, 7-oxabicyclo[4.1.1]-hept-3-ene, 8-oxabicyclo[3.2.1]heptane, 8-oxabicyclo[3.2.1]-hept-2-ene, 8-oxabicyclo[3.2.1]hept-3-ene, 8-oxabicyclo[3.2.1] hept-6-ene, etc.

The aromatic ring may be, for instance, any one having not more than 10 carbon atoms, of which specific examples are benzene and naphthalene.

The non-aromatic hydrocarbon ring represented by its both sides, i.e. $—(CH_2)_p—$ and $—(CH_2)_q—$, at the 1- and 1-positions, the 1- and 2-positions, the 1- and 3-positions, the 1- and 4-positions or the like.

The aromatic group represented by the symbol Ar may be monocyclic, bicyclic or the like and have usually not more than 10 carbon atoms, and its specific examples are phenyl, naphthyl, etc. The heterocyclic aromatic group represented by the symbol Ar may be also monocyclic, bicyclic or the like. The monocyclic heterocyclic aromatic group may be the one, for instance, having not more than 6 carbon atoms and not more than 4 hetero atoms chosen from nitrogen, oxygen and sulfur, and its specific examples are pyridyl, pyrimidinyl, thiazolyl, oxazolyl, isoxazolyl, isothiazolyl, furyl, imidazolyl, etc. The bicyclic heterocyclic aromatic group may be the one, for instance, having not more than 10 carbon atoms and not more than 5 hetero atoms chosen from nitrogen, oxygen and sulfur, and its specific examples are a benzologous condensed ring group (e.g. benzisothiazolyl, benzisoxazolyl, benzofuryl, quinolyl, isoquinolyl, indolyl, indazolyl, benzimidazolyl, benzoxazolyl), naphthyridinyl, pteridinyl, thienofuryl, imidazothiophenyl, imidazofuryl, etc.

The present invention covers the acid addition salt formed between the imide compound (I) and an organic or inorganic acid. Examples of the inorganic acid are hydrochloric acid, hydrobromic acid, hydroiodic acid, sulfuric acid, etc., and examples of the organic acid are acetic acid, oxalic acid, citric acid, malic acid, tartaric acid, maleic acid, fumaric acid, etc.

The imide compound (I) can have stereo and optical isomers, and this invention involves these isomers or their mixtures as well.

Among various groups represented by the symbol Ar, preferred are a bicyclic heterocyclic aromatic group, a naphthyl group, a benzoyl group, a phenoxy group, a phenylthio group, a biphenylmethylidene group, etc., these groups being optionally substituted with at least one of lower alkyl, lower alkoxy and halogen. More preferred are a benzologous condensed ring group, a naphthyl group, a benzoyl group, a phenoxy group, a phenylthio group, etc., these groups being optionally substituted with at least one of lower alkyl, lower alkoxy and halogen. The most preferred are benzisothiazolyl, benzisoxazolyl, indazolyl, indolyl, benzoyl, phenoxy, phenylthio, etc., which are optionally substituted with at least one of lower alkyl, lower alkoxy and halogen.

Preferred examples of the group represented by the symbol Z are those of the following formulas:

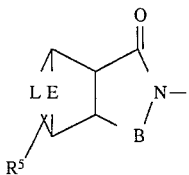
(Z-1)

wherein L is —CH$_2$—CH$_2$— or —CH=CH—, E is a lower alkylene group optionally substituted with lower alkyl or an oxygen atom, R$^5$ is a hydrogen atom or a lower alkyl group and B is a carbonyl group or a sulfonyl group,

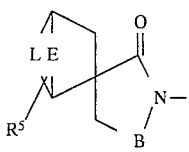
(Z-2)

wherein L, E, R$^5$ and B are each as defined above,

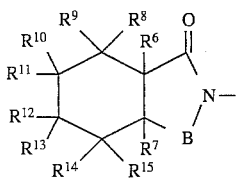
(Z-3)

wherein R$^6$, R$^7$, R$^8$, R$^9$, R$^{10}$, R$^{11}$, R$^{12}$, R$^{13}$, R$^{14}$ and R$^{15}$ are each a hydrogen atom or a lower alkyl group, or two of those present at the neighbouring positions each other may be combined together to make a bond (i.e. forming a double bond between said two positions) and B is as defined above;

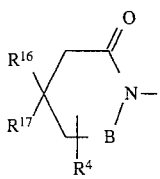
(Z-4)

wherein R$^{16}$ and R$^{17}$ are each a hydrogen atom or a lower alkyl group, or they may be taken together to make a saturated hydrocarbon ring, preferably a cycloalkane ring having not more than 7 carbon atoms (e.g. cyclopropane, cyclobutane, cyclopentane, cyclohexane, cycloheptane) and R$^4$ and B are each as defined above, and

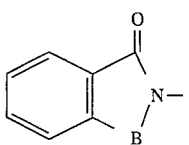
(Z-5)

wherein B is as defined above.

More preferred examples of the group represented by the symbol Z are those of the following formulas:

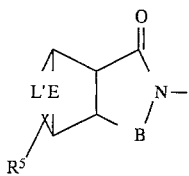
(Z-1')

wherein L' is —CH$_2$—CH$_2$— and E, R$^5$ and B are each as defined above,

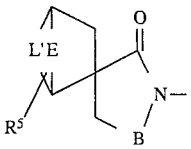
(Z-2')

wherein L', E, R$^5$ and B are each as defined above,

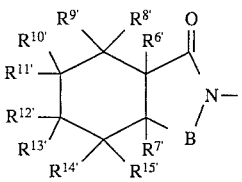
(Z-3')

wherein R$^{6'}$, R$^{7'}$, R$^{8'}$, R$^{9'}$, R$^{10'}$, R$^{11'}$, R$^{12'}$, R$^{13'}$, R$^{14'}$ and R$^{15'}$ are each a hydrogen atom or a lower alkyl and B is a defined above;

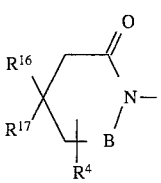
(Z-4')

wherein R$^4$, R$^{16}$, R$^{17}$ and B are each as defined above, and

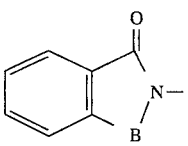
(Z-5')

wherein B is as defined above.

The imide compounds (I) of the invention are obtainable by various procedures, of which typical examples are as shown below.

Procedure (a):—

The imide compound (I) is obtainable according to the following scheme:

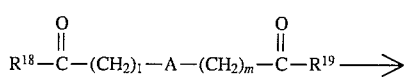

(II)

(III)

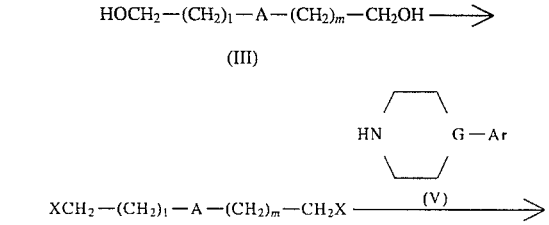

(IV)                          (V)

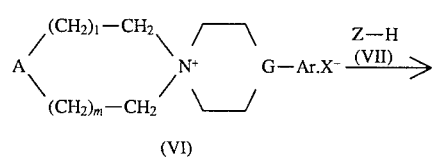

(VI)

7
-continued

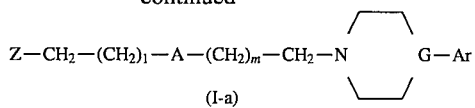

(I-a)

wherein A, G, Ar and Z are each as defined above and $R^{18}$ and $R^{19}$ are each a hydroxy group or a lower alkoxy group, or they may be taken together to represent an oxygen atom, X is a leaving group such as halogen, lower alkylsulfonyloxy (e.g. methanesulfonyloxy), arylsulfonyloxy (e.g. p-toluene-sulfonyloxy, benzenesulfonyloxy) and 1 and m are each an integer of 0 or 1.

Namely, the compound (II) is reduced to give the compound (III). The reduction may be carried out by treatment with a reducing agent (e.g. $LiAlH_4$, $H_4$, $NaBH_4$, $Ca(BH_4)_2$, $LiAlH_2(OCH_2CH_2OCH_3)_2$) in an inert solvent at a temperature of 0° C. to the reflux temperature of the reaction mixture to give the compound (III). The reducing agent is usually employed in an amount of about 1 to 10 mol to one mol of the compound (II). As the inert solvent, there may be used an ethereal solvent such as diethyl ether or tetrahydrofuran.

The hydroxy groups in the compound (III) are then converted respectively into leaving groups to give the compound (IV). When the leaving group is a halogen atom (e.g. chlorine, bromine), the conversion may be carried out by reacting the compound (III) with thionyl halide (e.g. thionyl chloride, thionyl bromide), optionally in the presence of a base (e.g. pyridine). This reaction is preferably performed in a solvent (e.g. pyridine, tetrahydrofuran, dichloromethane) at a temperature of about 0° to 30° C. The molar proportion of the compound (III) and thionyl halide may be usually about 1:2–4.

When the leaving group is sulfonyloxy, the conversion may be effected by reacting the compound (III) with a sulfonyl halide such as alkylsulfonyl halide (e.g. methanesulfonyl chloride) or arylsulfonyl halide (e.g. p-toluenesulfonyl chloride, benzenesulfonyl chloride), optionally in the presence of a base (e.g. triethylamine). This reaction is favorably performed in a solvent (e.g. pyridine, tetrahydrofuran, dichloromethane, chloroform) at a temperature of about 0° to 30° C. The molar proportion of the compound (III) and the sulfonyl halide is usually about 1:2–4.

The compound (IV) is then reacted with the compound (V) to give the compound (VI). The reaction may be carried out in the presence of a base (e.g. potassium carbonate, sodium carbonate) in a solvent such as alcohol (e.g. methanol, ethanol, propanol, 2-propanol, butanol), acetonitrile or dimethylformamide at a temperature around the boiling point of the solvent. The base and the compound (V) may be used respectively in amounts of about 0.5 to 2 mol and of about 1 to 1.5 mol to one mol of the compound (IV).

The compound (VI) is then reacted with the compound (VII) to give the compound (I-a). This reaction is carried out optionally in the presence of a catalyst and a base (e.g. potassium carbonate, sodium carbonate, sodium hydride, potassium hydride) in an aromatic solvent (e.g. toluene, xylene, chlorobenzene) at a temperature around the boiling point of the solvent. As the catalyst, a crown ether such as dibenzo-18-crown-6-ether may be used, and its amount is normally from about 0.1 to 10% by weight based on the compound (VI). The molar proportion of the compound (VI) and the compound (VII) to be used is usually about 1:1–1.5.

8

Procedure (b):—

The imide compound (I) is also produced according to the following scheme:

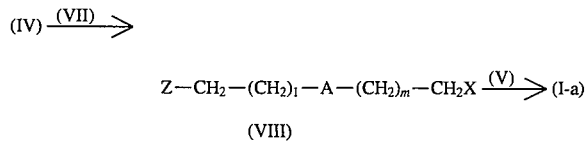

wherein X, A, Z, 1 and m are each as defined above.

The compound (IV) is reacted with the compound (VII) in the presence of a base such as an inorganic base (e.g. potassium carbonate, sodium carbonate, sodium hydride, potassium hydride) to give the compound (VIII). The reaction is usually carried out in a solvent (e.g. alcohol, dimethylformamide, acetonitrile); optionally in the coexistence of a reaction aid such as an alkali metal iodide (e.g. potassium iodide, sodium iodide), at a temperature around the boiling point of the solvent. The amounts of the base, the reaction aid and the compound (VII) may be respectively from about 1 to 2 mol, from about 0.1 to 1 mol and from about 0.1 to 1 mol to one mol of the compound (IV).

The compound (VIII) is then reacted with the compound (V) in the presence of a base (e.g. potassium carbonate, sodium carbonate, sodium hydride, potassium hydride) to give the compound (I-a). The reaction is normally carried out in a solvent (e.g. alcohol, dimethylformamide, acetonitrile), optionally in the coexistence of a reaction aid such as an alkali metal iodide (e.g. potassium iodide, sodium iodide), at a temperature around the boiling point of the solvent. The amounts of the base and the reaction aid may be respectively from about 1 to 2 mol and from about 0.1 to 1 mol to one mol of the compound (VIII). The molar proportion of the compound (VIII) and the compound (V) may be usually about 1:1–1.5.

Procedure (c):—

The imide compound (I) is further obtainable according to the following scheme:

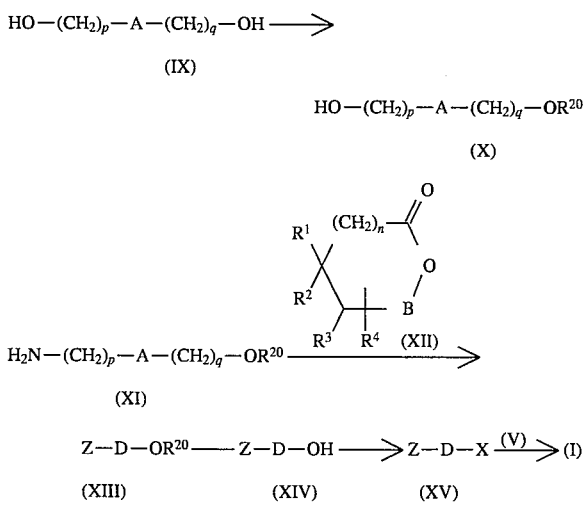

wherein $R^1$, $R^2$, $R^3$, $R^4$, n, p, q, D, A, B, X and Z are each as defined above and $R^{20}$ is a protective group for hydroxy (e.g. benzyl, halogen, methoxy or nitro-substituted benzyl, methoxymethyl, methoxyethoxymethyl, tetrahydrofuranyl).

The compound (IX) is converted into the compound (X) by application of a per se conventional protection procedure (g.g. T. W. Greene: "Protective Group in Organic Synthesis", John Willey & Sons, pages 10–39 (1981)) to the former. Examples of the protective group for hydroxy thus introduced are benzyl, substituted benzyl (e.g. halogen-, methoxy- or nitro-substituted benzyl), methoxymethyl, methoxyethoxymethyl, tetrahydrofuryl, etc.

The compound (X) is then subjected to oxidation, oximation (i.e. oxime formation) and reduction in this order to give the compound (XI). The oxidation may be carried out by reacting the compound (X) with an oxidizing agent such as chromic acid or its salt (e.g. chromic anhydride, bichromic acid). The oximation may be carried out by reacting the oxidized product with hydroxylamine in an alcohol at a temperature of about 0° to 30° C. Hydroxylamine is normally used in an amount of about 1 to 2 mol to one mol of the compound (X). The reduction may be carried out by reacting the oximated product with a reducing agent (e.g. lithium aluminum hydride) in an inert solvent (e.g. diethyl ether or tetrahydrofuran) at a temperature around the boiling point of the solvent. The amount of the reducing agent is usually from about 1 to 10 mol to one mol of the compound (X).

The compound (XI) thus obtained is reacted with the compound (XII) in a solvent (e.g. pyridine, toluene, xylene, chlorobenzene) at a temperature around the boiling point of the solvent to give the compound (XIII). The amount of the compound (XII) is ordinarily from about 1 to 3 mol to 1 mol of the compound (XI).

The compound (XIII) is then subjected to elimination of the protecting group by a per se conventional procedure (e.g. T. W. Greene: "Protective group in organic synthesis", John Wiley & Sons, pages 10–39 (1981)) to give the compound (XIV).

Conversion of the compound (XIV) into the compound (XV) is accomplished by introduction of a leaving group into the former. When the leaving group is halogen (e.g. chlorine, bromine), the compound (XIV) may be reacted with thionyl halide (e.g. thionyl chloride, thionyl bromide) in the presence of a base (e.g. pyridine) in a solvent (e.g. pyridine, tetrahydrofuran, dichloromethane) at a temperature of about 0° to 30° C. The amount of the thionyl halide is normally from about 2 to 4 mol to 1 mole of the compound (XIV).

When the leaving group is sulfonyloxy, the compound (XIV) is reacted with a sulfonyl halide such as alkylsulfonyl halide (e.g. methanesulfonyl chloride) or arylsulfonyl halide (e.g. benzenesulfonyl chloride, p-toluenesulfonyl chloride) in the presence of a base (e.g. triethylamine). This reaction is usually carried out in a solvent (e.g. pyridine, tetrahydrofuran, dichloromethane, chloroform) at a temperature of about 0° to 30° C. The amount of the sulfonyl halide is normally from about 2 to 4 mol to one mol of the compound (XIV).

The compound (XV) thus produced is reacted with the compound (V) in the presence of a base in the coexistence of a reaction aid to give the compound (I). The reaction is normally performed in a solvent (e.g. alcohol, dimethylformamide, acetonitrile) at a temperature around the boiling point of the solvent. As the base, there may be used an inorganic base (e.g. potassium carbonate, sodium carbonate, sodium hydride, potassium hydride). As the reaction aid, an alkali metal iodide (e.g. potassium iodide, sodium iodide) is usable. The amounts of the base, the reaction aid and the compound (V) are respectively from about 1 to 2 mol, from about 0.1 to 1 mol and from about 1 to 1.5 mol to one mol of the compound (XV).

Procedure (d):—

The imide compound (I) is further obtainable according to the following scheme:

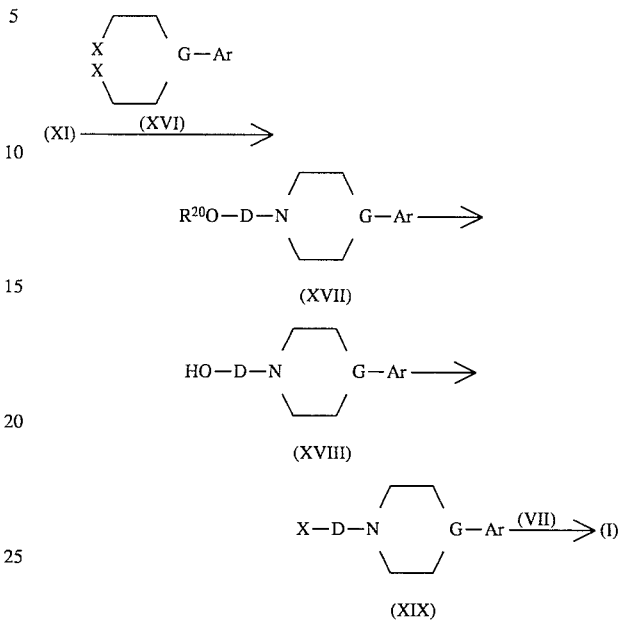

wherein $R^{20}$, D, G, X and Ar are each as defined above.

The compound (XI) is reacted with the compound (XVI) in the presence of a base in a solvent (e.g. alcohol, diglyme, toluene, chlorobenzene) at a temperature around the boiling point of the solvent to give the compound (XVII). As the base, there may be used an inorganic base (e.g. potassium carbonate, sodium carbonate), and its amount is normally from about 1 to 2 mol to one mol of the compound (XI). The compound (XVI) is used ordinarily in an amount of about 1 to 1.5 mol to one mol of the compound (XI).

The compound (XVII) is subjected to elimination of the protecting group by a per se conventional procedure (e.g. T. W. Greene: "Protective Group in Organic Synthesis", John Wiley & Sons, pages 10–39 (1981)) to give the compound (XVIII).

Introduction of a leaving group into the compound (XVIII) affords the compound (XIX). When the leaving group is halogen (e.g. chlorine, bromine), the compound (XVIII) is reacted with thionyl halide (e.g. thionyl chloride, thionyl bromide), optionally in the presence of a base (e.g. pyridine). The reaction is normally carried out in a solvent (e.g. pyridine, tetrahydrofuran, dichloromethane) at a temperature of about 0° to 30° C. The amount of the thionyl halide may be from about 2 to 4 mol to 1 mol of the compound (XVIII).

When the leaving group is sulfonyloxy, the compound (XVIII) is reacted with a sulfonyl halide such as an alkylsulfonyl halide (e.g. methanesulfonyl chloride) or an arylsulfonyl chloride (e.g. p-toluenesulfonyl chloride, benzenesulfonyl chloride), optionally in the presence of a base (e.g. triethylamine). The reaction is normally carried out in a solvent (e.g. pyridine, tetrahydrofuran, dichloromethane, chloroform) at a temperature of about 0° to 30° C. The amount of the sulfonyl halide may be from about 2 to 4 mol to one mol of the compound (XVIII).

The compound (XIX) is reacted with the compound (VII) in the presence of a base (e.g. potassium carbonate, sodium carbonate, sodium hydride, potassium hydride) in a solvent (e.g. alcohol, acetonitrile, dimethylformamide) at a temperature around the boiling point of the solvent to give the compound (I). The amounts of the base and the compound (VII) may be respectively from about 0.5 to 2 mol and from about 1 to 1.5 mol to 1 mol of the compound (XIX).

The products in Procedures (a) to (d), i.e. the compounds (I) and (I-a), may be each purified by a per se conventional procedure such as recrystallization from a suitable solvent (e.g. alcohol, diethyl ether, ethyl acetate, hexane) or chromatography on a column of silica gel. It is also possible to convert the products into their acid addition salts and then purify by recrystallization from a proper solvent (e.g. acetone, diethyl ether, alcohol).

Throughout Procedures (a) to (d), the introduction of a protective group is accomplished by a per se conventional procedure. When, for instance, the protective group is benzyl, substituted benzyl (e.g. halogen-, methoxy- or nitro-substituted benzyl) or methoxymethyl, the starting compound into which the protective group is to be introduced may be reacted with a protective group-introducing reagent such as benzyl halide, substituted benzyl halide or methoxymethyl halide in the presence of a basic substance such as an alkali metal hydride (e.g. sodium hydride, potassium hydride) or an organic base (e.g. triethylamine, dimethylaminopyridine) in an organic solvent (e.g. tetrahydrofuran, dimethylformamide) at a temperature of about $-10°$ to $30°$ C. The amount of the protective group-introducing reagent may be from about 1 to 2 mol to one mol of the starting compound.

Elimination of the protective group may be also carried out by a per se conventional procedure. When, for instance, the protective group is benzyl or substituted benzyl, the elimination may be effected by hydrogenation using a noble metal catalyst (e.g. Pd-C, PtO, Pt-C) under a hydrogen pressure of 1 to 3 atm. When the protective group is benzyl, substituted benzyl or methoxymethyl, the elimination may be accomplished by treatment with a strong acid (e.g. $CF_3COOH$, HBr, $HBr-CH_3COOH$).

Optical resolution of the compound (I) can be accomplished by dissolving in an inert solvent (e.g. acetonitrile, alcohol), adding an optically active acid thereto to form the optically active salt between the compound (I) and the acid, precipitating the formed salt, collecting the precipitated salt and treating the collected salt with a base to make the optically active compound (I) in a free form.

As the optically active acid, there may be used, for instance, L-tartaric acid, D-tartaric acid, D-camphanic acid, L-mandelic acid, L-pyroglutamic acid, D-10-CSA (D-10-camphor-sulfonic acid), D-quinic acid, L-malic acid, dibenzoyl-L-tartaric acid, etc., among which preferred are L-tartaric acid and D-tartaric acid. No particular limitation is present on the temperature at which the salt formation is to be carried out, and the salt formation may be effected within a wide range from room temperature to the refluxing temperature of the reaction system. For enhancement of the optical purity, however, it is favored that the reaction system is once heated to the refluxing temperature. Before collection of the precipitated salt by filtration, the mixture may be once cooled so as to increase the yield. The amount of the optically active acid as the resolving agent may be from 0.5 to 2.0 equivalents, preferably around one equivalent, to the substrate. When desired, the collected salt may be recrystallized from a proper solvent such as alcohol to give the optically active salt with a higher purity. The thus obtained salt may be treated with a base to release an optical isomer of the compound (I) in a free form.

For the therapeutic use as an antipsychotic agent, the imide compound (I) or its pharmaceutically acceptable salt may be used as such, but it is usually formulated into a pharmaceutical preparation such as tablets, capsules, syrups, suspension, solutions, emulsions and suppositories by a per se conventional procedure. Depending upon the administration route such as parenteral or non-parenteral administration (e.g. oral administration, intravenous administration, rectal administration), an appropriate preparation form may be employed. In order to make said pharmaceutical preparation, the imide compound (I) or its pharmaceutically acceptable salt may be combined, if necessary, with any suitable additive(s) such as carriers, diluents, filters, binders and stabilizers. In case of an injectionable preparation, pharmaceutically acceptable buffers, solubilizers, isotonizers, etc. may be incorporated therein.

While the dosage of the imide compound (I) or its pharmaceutically acceptable salt varies greatly with the symptom, age and weight of the patient, the dosage form, the administration mode and the like, it may be generally given to an adult at a daily dose of from about 1 to 1000 mg, preferably from about 5 to 100 mg, in case of oral administration and at a daily dose of from about 0.1 to 100 mg, preferably from about 0.3 to 50 mg, in case of intraveous injection. Said dose may be applied in a single time or dividedly in two or more times.

As stated above, the imide compound (I) and its pharmaceutically acceptable salts exert a significant anti-psychotic activity. Yet, they are very weak in side effects as observed on the conventional neuroleptic drugs.

The above facts are well evidenced by the pharmacological test data as set forth below.

(i) Dopamine $D_2$ receptor binding assay (in vitro)

It is known that there is a correlation between the antipsychotic activity and the dopamine $D_2$ receptor binding activity. This assay is therefore to examine an affinity of the test compound to dopamine $D_2$ receptor in membrane fractions of corpus striatum taken out from rat brain according to the method as described in T. Kuno et al: J. Neurochem., 41, 841 (1983).

Fresh corpus striatum taken out from rat brain is homogenized in a 30-fold volume of Tris-HCl buffer solution (pH, 7.4; 0.05 M) and centrifuged (31,360×g) for 10 minutes to give the membrane fractions, which are washed with the same volume of the buffer solution twice to give the membrane fractions for assay.

The membrane fractions as above obtained (containing 5 mg of protein) are incubated at 37° C. for 30 minutes in a buffer solution comprising [$^3$H] raclopride (0.45 nM), sodium chloride (120 mM), 1 mM magnesium chloride, 5 mM potassium chloride, 2 mM calcium chloride, Tris-HCl (pH, 7.4; 50 mM), 0.01% ascorbic acid, 1 mM pargyline and the test compound ($10^{-9}$ to $10^{-5}$ M). Upon termination of the reaction, the membrane fractions are collected through a Whatman GF/B glass filter and number of [$^3$H] raclopride bound to membranes is measured by the aid of a liquid scintillation counter. Number of [$^3$H] raclopride binding specific to the $D_2$ receptor in a designed concentration of the test compound is calculated according to the following equation and the $IC_{50}$ and Ki are determined on the basis of a hill plot according to the method as described in Life Sci., .23, 1781–1784 (1978). As the representative anti-phychotic drug, Haloperidol is used as control.

Number of specific binding=

(Total number of bindings)—(Number of non-specific bindings, e.g. number of bindings in co-existence of $10^{-6}$ M (+)Butaclamol)

Ki (nM)=$IC_{50}/(1+S/K_D)$

S: concentration of [$^3$H] raclopride on assay $K_D$: dissociation constant of [$^3$H] raclopride
The results are shown in Table 2.

TABLE 2

| Compound No. | Ki (nM) |
|---|---|
| 101 | 1.6 |
| 105 | 1.0 |
| Haloperidol | 0.57 |

Further, the anti-psychotic activity (e.g. inhibition of [$^3$H] raclopride binding to $D_2$ receptors) of the designated compound at the concentration of 0.01 μM is observed, of which the results are shown in Table 3.

TABLE 3

| Compound No. | Antipsychotic activity (% inhibition) |
|---|---|
| 101 | 60 |
| 106 | 90 |
| 107 | 71 |
| 161 | 24 |
| 163 | 11 |

(ii) Anti-climbing activity (in vivo)

This activity is examined through the anti-climbing behavior test, i.e. the test for suppressing the climbing behavior induced by apomorphine in mice.

A designed amount of the test compound is orally administered to several groups of ddY strain male mice (bodyweight, 20 to 25 g; one group, 5 mice), and each of the animals is placed in an individual column cage of 12 cm in diameter and 14 cm in height having metal poles (each pole, 2 mm in diameter) vertically installed and arranged along the periphery with intervals of 1 cm. After 60 minutes, apomorphine (1.0 mg/kg) is subcutaneously injected, and the behavior is observed during 10 to 20 minutes. Evaluation is made on the basis of the following criteria [P. Protais et al.: Psychopharmacology, 50, 1–6 (1976)]:

| Score | Evaluation |
|---|---|
| 0 | All the paws are on the floor |
| 1 | only forepaws seize the pole of the cage |
| 2 | All the paws seize the pole of the cage; climbing behavior observed discontinuously |
| 3 | Continuous climbing behavior observed |

Inhibition percentage of climbing behavior per each dose is calculated by the following equation, and $ED_{50}$ (50% suppressive dose) is determined thereon:

$$\text{Inhibition percentage (\%)} = \frac{\text{Total score in control group} - \text{Total score in tested group}}{\text{Total score in control group}} \times 100$$

The results are shown in Table 4 in which the representative psychotic drugs such as Haloperidol and Chlorpromazine are used for control.

TABLE 4

| Compound No. | $ED_{50}$ (mg/Kg) |
|---|---|
| 101 | 10.3 |
| 107 | 26.5 |
| Haloperidol | 0.67 |
| Chlorpromazine | 4.2 |

(iii) Side-effect
a) Catalepsy inducing activity

The catalepsy inducing activity, which is the typical central nervous system side-effect, i.e. extrapyramidal side-effect, on clinical use of the psychotic drug, is observed.

A designated amount of the test compounds is orally administered to male mice, and one hour later a pair of forepaws are forcedly hanged on an iron pipe (diameter, 2.5 mm) horizontally set at a height of 5 cm. At least one cataleptic state of more than 30 second per three trials is regarded as positive. The results are shown in Table 5.

TABLE 5

| Test compound | $ED_{50}$ (mg/kg) | Ratio to anti-apomorphine activity |
|---|---|---|
| Compound No. 101 | 747 | 72.5 |
| Haloperidol | 3.1 | 4.6 |
| Chlorpromazine | 18 | 4.3 |

Ptosis inducing activity

Since the blocking activity of $\alpha_1$ adrenergic receptor inherent to the anti-psychotic drug has a correlation with cardiovascular organ side-effect such as orthostatic hypotension, a ptosis inducing test is conducted to evaluate the $\alpha_1$-receptor blocking activity.

The designated compound is orally administered to mice and after one hour blepharoptosis is scored, of which the results are shown in Table 6.

TABLE 6

| Test compound | $ED_{50}$ (mg/kg) | Ratio to anti-apomorphine activity |
|---|---|---|
| Compound No. 101 | >1000 | >97 |
| Haloperidol | 4.1 | 6.0 |
| Chlorpromazine | 6.0 | 1.4 |

The above pharmacological data support that the imide derivatives (I) and their acid addition salts according to the invention show an excellent anti-psychotic activity. Further, the efficacy ratio of the anti-psychotic activity (i.e antiapomorphine activity) to the side-effect induction reveals that they have least central and peripheral nervous system side-effects in comparison with the conventional drugs.

Practical and presently preferred embodiments of the invention are illustratively shown in the following Examples wherein the abbreviations have the following meanings: Ms, methanesulfonyl; Et, ethyl; Ph, phenyl.

Reference Example 1-(a)

Production of trans-3a,7a-octahydroisoindolium-2-spiro-1'-[4'-(1,2-benzisothiazol- 3-yl)]piperazine methanesulfonate (Compound No. 201 ):-

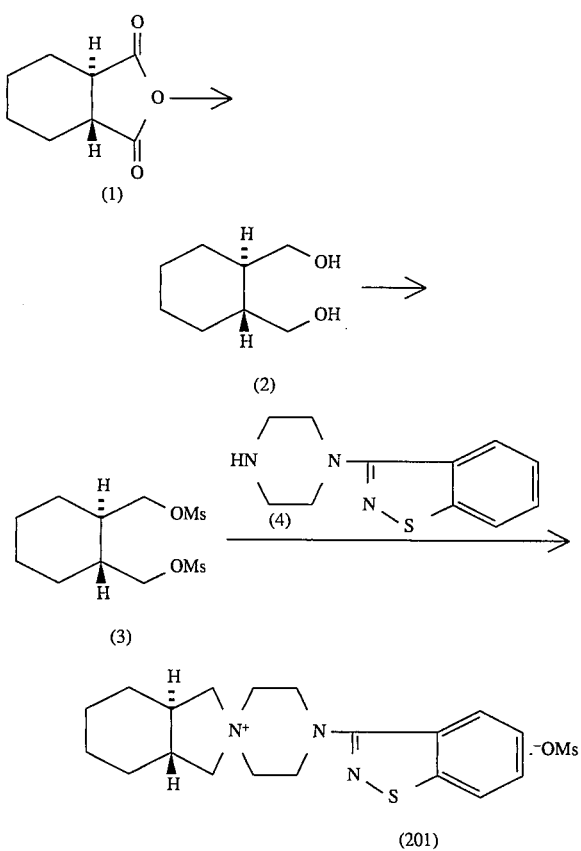

To a mixture of lithium aluminum hydride (2.85 g; 75 mmol) and diethyl ether (50 ml), a solution of trans-1,2-cyclohexanedicarboxylic acid anhydride (1) (7.71 g; 50 mmol) in diethyl ether (150 ml) is dropwise added, and the resultant mixture is allowed to react at room temperature for 3 hours and then heated under reflux for 2 hours. After cooling, wet ether is dropwise added to the reaction mixture, followed by addition of water. The organic layer is collected by decantation, followed by concentration to give trans-1,2-bis(hydroxymethyl)cyclohexane (2) (5.1 g).

The thus obtained compound (2) (5.1 g; 35.4 mmol) is dissolved in triethylamine (10.37 g; 103 mmol) and acetonitrile (127 ml), and methanesulfonyl chloride (8.13 g; 71 mmol) is dropwise added thereto under ice-cooling. The resultant mixture is ice-cooled for 1 hour and allowed to react at room temperature for 3 hours. The reaction mixture is washed with water, dried and concentrated, followed by addition of diethyl ether. Precipitated crystals are collected by filtration to give trans-1,2-bis(methanesulfonyloxymethyl)cyclohexane (3) (5.4 g).

A mixture of the compound (3) (3.06 g; 10.2 mmol), 3-(1-piperazinyl-1,2-benzisothiazole (4) (2.19 g; 10 mmol), sodium carbonate (1.05 g; 10 mmol) and acetonitrile (45 ml) is refluxed for 23 hours. The reaction mixture is filtered while hot, and the filtrate is concentrated to give the objective compound (Compound No. 201) (4.3 g). m.p., 220°–225° C.

Reference Example 1-(b)

Production of trans-1,2-bis (methanesulfonyloxymethyl) cyclohexane (3):—

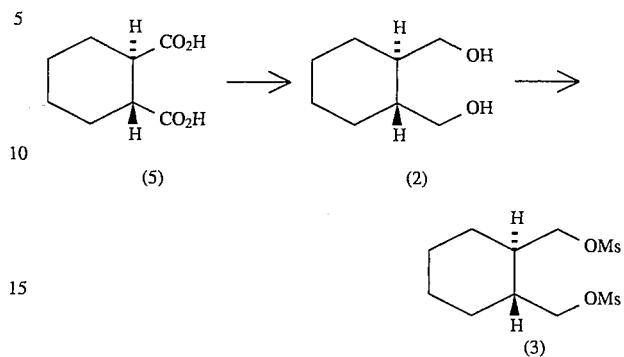

To a mixture of lithium aluminum hydride (52.22 g; 1,374 mol) and tetrahydrofuran (500 ml), a solution of trans-1,2-cyclohexanedicarboxylic acid (5) (118.18 g; 0.687 mol) in tetrahydrofuran (2 liters) is dropwise added under reflux, and the resultant mixture is allowed to react under reflux for 3 hours. After completion of the reaction, the reaction mixture is cooled, and wet tetrahydrofuran and ether are dropwise added thereto, followed by filtration. The filtrate is concentrated under reduced pressure to give trans-1,2-bis(hydroxymethyl)cyclohexane (2) (71.86 g).

To a solution of the compound (2) (71.86 g; 0.499 mol) and triethylamine (151.21 g; 1.497 mol) in chloroform (1 liter), methanesulfonyl chloride (114.27 g; 0.998 mol) is dropwise added under ice-cooling, and the resultant mixture is stirred at room temperature for 6 hours. The reaction mixture is washed with water, dried and concentrated under reduced pressure. Diethyl ether is added to the residue for crystallization, and the precipitated crystals are collected to give trans-1,2-bis(methanesulfonyloxymethyl)cyclohexane (3) (88.57 g).

Reference Example 2

Production of N-[(2-chloromethyl)cyclopropylmethyl]cyclohexane-1,2-dicarboximide (Compound No. 202):—

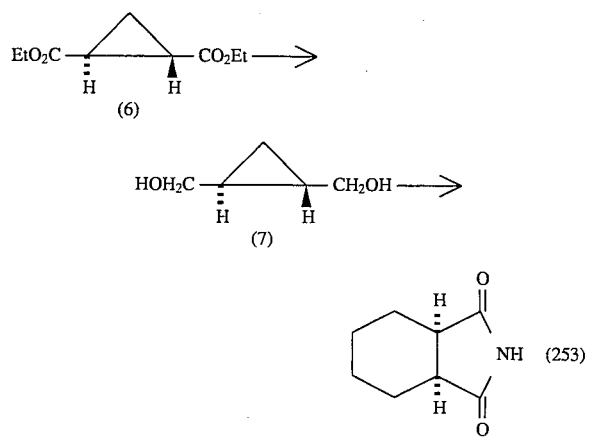

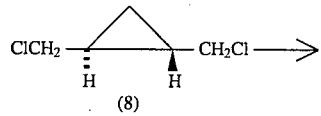

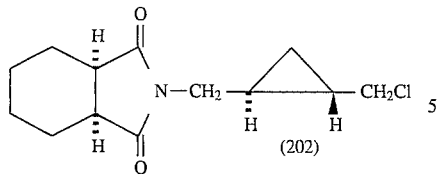

To a mixture of lithium aluminum hydride (6.65 g; 175 mmol) and diethyl ether (1000 ml), a solution of diethyl 1,2-cyclopropanedicarboxylate (6) (25.0 g; 134 mmol) in diethyl ether (250 ml) is dropwise added, and the resultant mixture is refluxed for 5 hours, followed by cooling. Wet ether is dropwise added to the reaction mixture, followed by addition of water. The organic layer is collected by decantation and dried. Concentration under reduced pressure gives 1,2-bis(hydroxymethyl)cyclopropane (7) (24.8 g).

To a solution of the compound (7) (3.0 g; 29.4 mmol) in pyridine (4.64 g), thionyl chloride (10.5 g; 88.2 mmol) is dropwise added, and the resultant mixture is stirred at a temperature of 0° to 5° C. for 30 minutes and at room temperature for 2 hours. The reaction mixture is concentrated, and to the residue diethyl ether and ethyl acetate (1:1) are added. After filtration of insoluble materials, the filtrate is concentrated to give 1.2-bis(chloromethyl)cyclopropane (8) (2.51 g).

$^1$H-NMR (CDCl$_3$) δ: 6: 0.75 (2 H, m), 1.25 (2 H, m), 3.45 (4 H, m).

A mixture of the compound (8) (0.3 g; 2.2 mmol), cyclohexane-1,2-dicarboximide (253) (66 rag; 0.43 mmol), potassium carbonate (0.3 g; 2.2 mmol), potassium iodide (0.3 g; 1.8 mmol) and acetonitrile (20 ml) is refluxed for 5 hours, and the reaction mixture is, after cooling, concentrated under reduced pressure. Chloroform is added to the residue, which is washed with water, dried, concentrated under reduced pressure and chromatographed on a silica gel column to give the objective compound (Compound No. 202) (0.11 g).

$^1$H-NMR (CDCl$_3$) δ: 0.60 (2 H, m), 0.95 (2 H, m), 1.45 (4 H, m), 1.85 (4 H, m), 2.85 (2 H, m), 3.20 (2 H, m), 3.55 (2 H, m).

Reference Example 3

Production of N-(3-methanesulfonyloxymethylcyclohexyl) bicyclo[2.2.1]heptane-2-exo-3-exo-dicarboximide (Compound No. 203):-

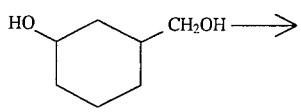

(9)

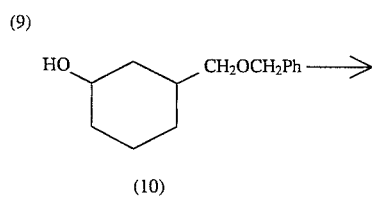

(10)

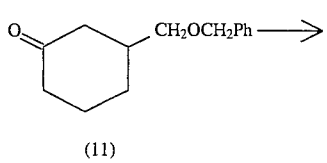

(11)

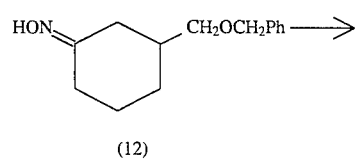

(12)

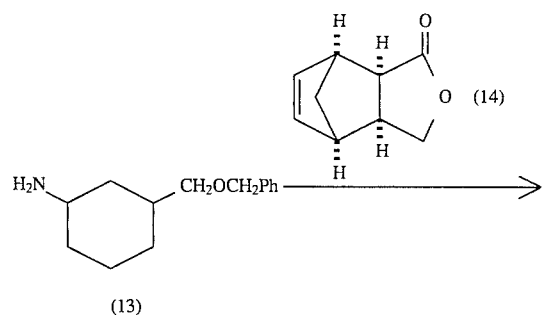

(13) (14)

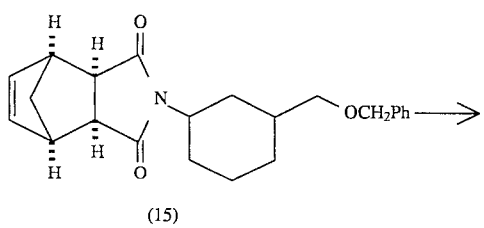

(15)

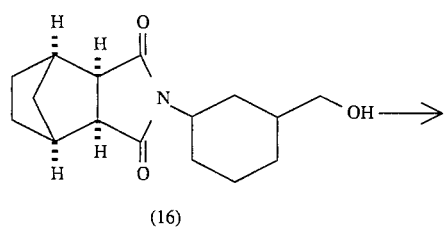

(16)

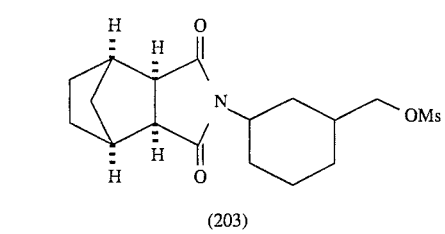

(203)

50% Sodium hydride (5.77 g; 120 mmol) is washed with n-hexane, and dimethylformamide (50 ml) is added thereto. To the resultant mixture, 3-hydroxymethylcyclohexanol (9) (10.0 g; 76.8 mmol) is dropwise added under ice-cooling, and then benzyl bromide (13.15 g; 76.8 mmol) is dropwise added thereto under ice-cooling. The resulting mixture is stirred at a temperature of 0° to 10° C. for 5 hours. The reaction mixture is poured into ice-water, extracted with toluene. The organic layer is washed with water, dried and concentrated under reduced pressure. The residue is chromatographed on a silica gel column to give 3-benzyloxymethylcyclohexanol (10) (9.55 g).

$^1$H-NMR (CDCl$_3$) δ: 0.8–2.1 (9 H, m), 3.35 (2 H, s), 3.60 (1 H, m), 4.50 (2 H, s), 7.35 (5 H, m).

To a solution of the compound (10) (4.9 g; 22.2 mmol) in acetone (90 ml), Jones reagent (chromic anhydride acid-sulfuric acid) (0.07 mol) is dropwise added, and the resultant mixture is stirred at a temperature of 0° to 10° C. for 2 hours. Methanol is dropwise added to the reaction mixture, which is poured into ice-water and extracted with chloroform. The extract is washed with water, dried and concentrated under reduced pressure. The residue is chromatographed on a silica gel column to give 3-benzyloxymethylcyclohexanone (11).

$^1$H-NMR (CDCl$_3$) δ: 1.15–2.50 (9 H, m), 3.38 (2 H, d), 4.50 (2 H, s), 7.30 (5 H, m).

To a solution of the compound (11) (1.0 g; 4.6 mmol), in ethanol (25 ml), sodium acetate (0.754 g; 9.2 mmol) and hydroxylamine hydrochloride (0.384 g; 5.5 mmol) are added, and the resultant mixture is stirred at room temperature for 3 hours. The reaction mixture is poured into ice-water, extracted with chloroform, washed with water and dried. After concentration under reduced pressure, the residue is chromatographed on a silica gel column to give 3-benzyloxymethylcyclohexanone oxime (12) (0.8 g).

$^1$H-NMR (CDCl$_3$) δ: 1.2–1.55 (2 H, m), 1.65–2.15 (5 H, m), 2.45 (1 H, m), 3.25 (1 H, m), 3.38 (2 H, m), 4.50 (2 H, s), 7.30 (5 H, m).

To a solution of the compound (12) (0.75 g; 3.2 mmol) in diethyl ether (30 ml), lithium aluminum hydride (0.75 g; 20 mmol) is added, and the resultant mixture is refluxed for 3 hours. After cooling, wet ether is dropwise added to the reaction mixture, and the organic layer is collected by decantation and dried, followed by concentration under reduced pressure to give 3-benzyloxymethylcyclohexylamine (13) (0.61 g).

$^1$H-NMR (CDCl$_3$) δ: 0.8–2.2 (9 H, m), 3.15 (1 H, s), 3.20 (1 H, s), 3.35 (2 H, m), 4.50 (2 H, s), 7.30 (5 H, m).

To a solution of the compound (13) (0.57 g; 2.6 mmol) in pyridine (30 ml), bicyclo[2.2.1]hept-5-ene-2-exo-3-exo-dicarboxylic acid anhydride (14) (854 rag; 5.2 mmol) is added, and the resultant mixture is refluxed for 7 hours. Pyridine is removed under reduced pressure, and chloroform is added to the residue and washed with water. The thus obtained residue is chromatographed on a silica gel column and further on a silica gel thin layer to give N-(3-benzyloxymethylcyclohexyl) bicyclo[2.2.1]hept-5-ene-2-exo-3-exodicarboximide (15) (0.23 g).

$^1$H-NMR (CDCl$_3$) δ: 0.9–2.45 (11 H, m), 2.60 (2 H, s), 3.25 (2 H, s), 3.30–3.52 (2 H, m), 4.00 (1 H, m), 4.55–4.65 (2 H, m), 6.30 (2 H, s), 7.30 (5 H, m).

To a solution of the compound (15) (0.21 g; 57.5 mmol) in methanol (10 ml), one drop of conc. hydrochloric acid and 10% palladium-carbon (210 mg) are added at room temperature to perform catalytic reduction. After completion of the reaction, the catalyst is removed. Removal of methanol under reduced pressure gives N-(3-hydroxymethylcyclohexyl) bicyclo[2.2.1]hept-2-exo-3-exo-dicarboximide (16) quantitatively.

H-NMR (CDCl$_3$) δ: 0.9–2.25 (15 H, m), 2.55 (2 H, s), 2.70 (2 H, s), 3.68 (2 H, brs), 4.08 (1 H, brs).

To a solution of the compound (16) (133 rag; 0.61 mmol) in pyridine (5 ml), methanesulfonyl chloride (82.4 mg; 0.92 mmol) is dropwise added under ice-cooling, and the resultant mixture is stirred at room temperature for 1.5 hours. Pyridine is removed under reduced pressure, and chloroform is added to the residue and washed with water. The chloroform solution is dried and concentrated under reduced pressure to give the objective compound (Compound No. 203).

H-NMR (CDCl$_3$) δ: 1.0–2.2 (15 H, m), 2.55 (2 H, s), 2.70 (2 H, s), 3.00 (3 H, s), 4.02 (3 H, m).

Reference Example 4

Production of Compound No. 204:-

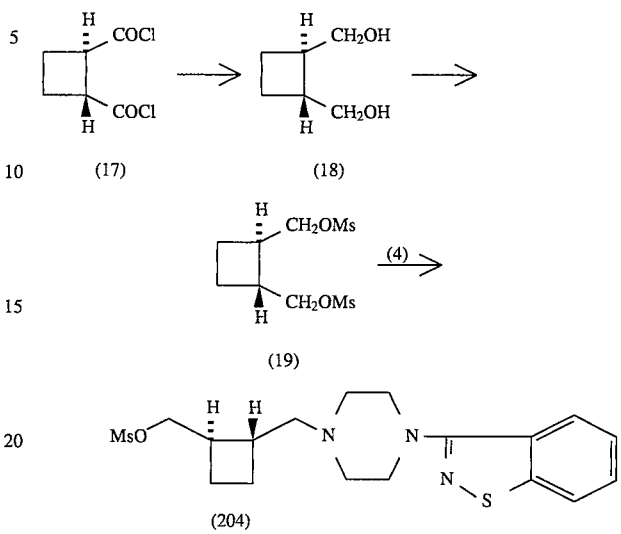

To a mixture of lithium aluminum hydride (11.86 g; 0.312 tool) and diethyl ether (300 ml), a solution of trans-1,2-bis(chlorocarbonyl)cyclobutane (17) (18.90 g; 0.104 mol) in diethyl ether (200 ml) is dropwise added under reflux, and the resultant mixture is refluxed for 3 hours. After cooling, wet tetrahydrofuran is dropwise added to the reaction mixture, followed by filtration. The filtrate is concentrated under reduced pressure to give trans-1,2-bis-(hydroxymethyl)cyclobutane (18) (8.76 g).

To a solution of the compound (18) (8.50 g; 0.0733 mol) and triethylamine (22.20 g; 0.22 mol) in chloroform (100 ml), methanesulfonyl chloride (16.79 g; 0.147 tool) is dropwise added under ice-cooling, and the resultant mixture is stirred for 7 hours at room temperature. The reaction mixture is washed with water, dried and concentrated under reduced pressure to give trans-1,2-bis (methanesulfonyloxymethyl)cyclobutane (19) (18.50 g). m.p., 60° to 62° C. (crystallized from ether).

A mixture of the compound (19) (10.00 g; 0.0368 tool), 3-(1-piperazinyl)-1,2-benzisothiazole (4) (7.25 g; 0.0331 mol), sodium carbonate (3.90 g; 0.0368 mol) and acetonitrile (300 ml) is refluxed for 13 hours, and the reaction mixture is cooled, followed by filtration. The filtrate is concentrated under reduced pressure and chromatographed on a silica gel column to give the objective compound (Compound No. 204) (2.84 g ).

$^1$H-NMR (CDCl$_3$) δ: 1.5–2.15 (4 H, m), 2.3–2.69 (8 H, m), 3.02 (3 H, s), 3.54 (4 H, t, J=5 Hz), 4.25 (2 H, d, J=5.6 Hz), 7.32–7.50 (2 H, m), 7.83–7.92 (2 H, m).

Reference Example 5

Production of Compound No. 205:-

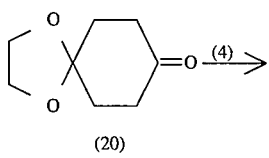

(20)

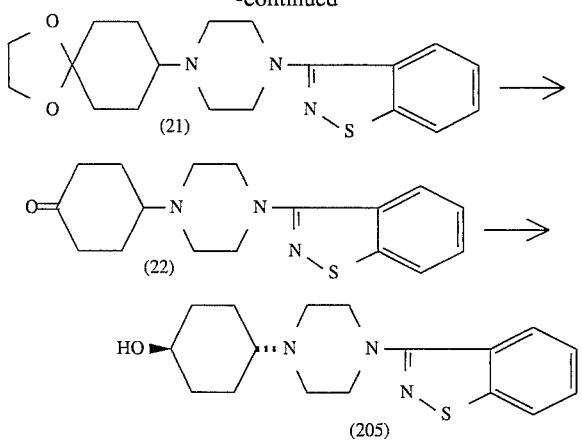

A mixture of 3-(1-piperazinyl)-1,2-benzisothiazole (4) (12.7 g; 0.058 mol), 1,4-cyclohexanedione monoethylene ketal (20) (10 g; 0.064 mol), p-toluenesulfonic acid (0.55 g; 0.0029 mol) and toluene (200 ml) is refluxed for 7 hours, and potassium carbonate (0.8 g; 0.0058 mol) is added thereto at room temperature. The resultant mixture is stirred for 1 hour and concentrated under reduced pressure. To the residue tetrahydrofuran (250 ml), methanol (20 ml) and sodium borohydride (2.19 g; 0.058 mol) are added, followed by stirring at room temperature for 15 hours. The reaction mixture is concentrated under reduced pressure, followed by addition of chloroform. The resultant solution is washed with water and dried. The solution is concentrated under reduced pressure and chromatographed on a silica gel column to give the compound (21) (1.57 g). m.p., 105° to 106° C.

A solution of the compound (21) (2.5 g; 0.007 mol) in 1 N hydrochloric acid (20 ml) and tetrahydrofuran (20 ml) is refluxed for 10 hours, and the reaction mixture is concentrated under reduced pressure. The residue is made alkali with aqueous potassium carbonate, extracted with ethyl acetate, dried and concentrated under reduced pressure to give the compound (22) (2.06 g).

To a solution of the compound (22) (2 g; 0.0063 tool) in methanol (200 ml), sodium borohydride (0.24 g; 0.0063 mol) is added under ice-cooling, followed by stirring for 30 minutes. The reaction mixture is concentrated under reduced pressure, followed by addition of water and extraction with ethyl acetate. The extract is dried and concentrated under reduced pressure to give the objective compound (Compound No. 205). m.p., 155° to 160° C.

$^1$H-NMR (CDCl$_3$) δ: 1.2–2.1 (9 H, m), 2.3–2.45 (1 H, m), 2.7–2.85 (4 H, m), 3.5–3.7 (5 H, m), 7.32–7.5 (2 H, m), 7.81 (1 H, d, J=8 Hz), 7.91 (1 H, d, J=8 Hz).

Reference Example 6

In the same manner as in Reference Examples 1 to 5, the compounds as shown in Table 7 are obtainable.

TABLE 7

| Compound No. | Structure | Physical constant | |
|---|---|---|---|
| 206 | 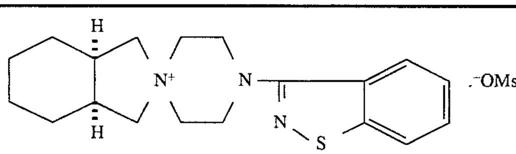 | Melting point: | 222–225° C. |
| 207 | 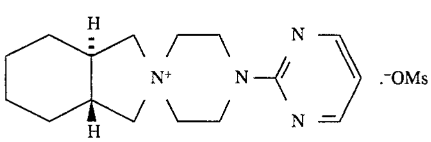 | Melting point: $^1$H-NMR (CDCl$_3$) δ: | 269–272° C. 1.2–1.4(4H, m), 1.7–2.2(6H, m), 2.70(3H, s), 3.35(2H, t, J=12Hz), 3.6–3.9(4H, m), 4.0–4.3(6H, m), 6.63(1H, t, J=5Hz), 8.33(2H, d, J=5Hz). |
| 208 Note: not isolated. | | | |
| 209 | 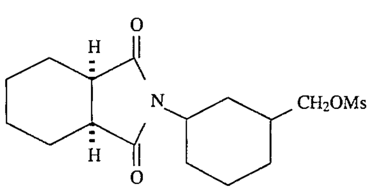 | $^1$H-NMR (CDCl$_3$) δ: EI-MS m/e: | 1.0–2.2(17H, m), 2.80(2H, m), 3.05(3H, s), 4.05(3H, m). 343 (M$^+$) |
| 210 | 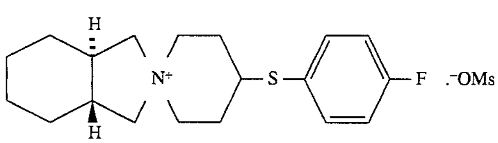 | Melting point: $^1$H-NMR (CDCl$_3$) δ: | 193–195° C. 1.1–1.4(4H, m), 1.65–2.0(8H, m), 2.1–2.3(2H, m), 2.72(3H, s), 2.93(1H, t, J=11Hz), 3.25 (1H, t, J=11Hz), 3.4–3.65(3H, m), 3.74(1H, dd, J=6 and 11Hz), 3.9–4.2(3H, m), 6.9–7.1(2H, m), 7.3–7.5(2H, m). |

TABLE 7-continued

| Compound No. | Structure | Physical constant | |
|---|---|---|---|
| 211 | 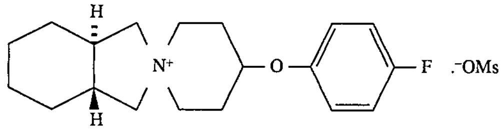 | Melting point: $^1$H-NMR (CDCl$_3$) δ: | 182–184° C. 1.1–1.5(4H, m), 1.7–2.2(8H, m), 2.25–2.55(2H, m), 2.74(3H, s), 3.10(1H, t, J=11Hz), 3.27 (1H, t, J=11Hz), 3.5–3.7(1H, m) , 3.75–3.9(1H, m), 3.9–4.1 (1H, m), 4.1–4.25(1H, m), 4.77 (1H, m), 6.85–7.0(4H, m). |
| 212 | 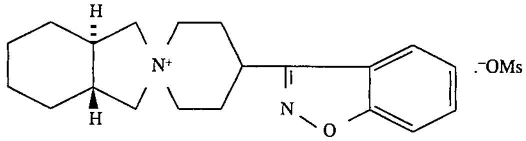 | Melting point: $^1$H-NMR (CDCl$_3$) δ: | 178–180° C. 1.1–1.45(4H, m), 1.7–2.05(6H, m), 2.05–2.35(2H, m), 2.35– 2.6(2H, m), 2.79(3H, s), 2.97 (1H, t, J=12Hz), 3.30(1H, t, J=12Hz), 3.54(1H, dd, J=13 and 26Hz), 3.87(1H, dd, J=6 and 12Hz), 4.0–4.2(1H, m), 4.26(1H, dd, J=6 and 12Hz), 4.4–4.6(1H, m), 7.07(1H, dt, J=2 and 7Hz), 7.19(1H, dd, J=2 and 8Hz), 7.91(1H, dd, J=5 and 9Hz). |
| 213 | 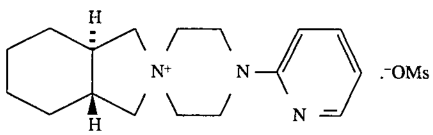 | Melting point: $^1$H-NMR (CDCl$_3$) δ: | 223–225° C. 1.15–1.45(4H, m), 1.7–2.2 (6H, m), 2.71(3H, s), 3.32(2H, t, J=12Hz), 3.65–4.1(10H, m), 6.65–6.8(2H, m), 7.52(1H, m), 8.15(1H, m). |
| 214 | 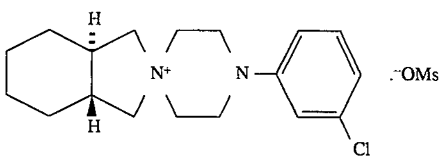 | Melting point: $^1$H-NMR (CDCl$_3$) δ: | 164–167° C. 1.1–1.4(4H, m), 1.75–2.2 (6H, m), 2.74(3H, s), 3.31(2H, t, J=2Hz), 3.45–3.65(4H, m), 3.75–3.95(4H, m), 4.0(1H, dd, J=2 and 11Hz), 6.75–7.0(3H, m), 7.15–7.2(1H, m). |
| 215 | 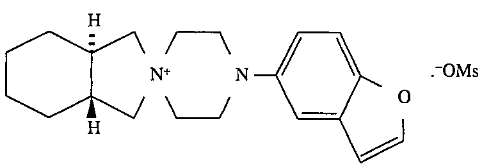 | Melting point: $^1$H-NMR (CDCl$_3$) δ: | 176–179° C. 1.27(4H, m), 1.7–2.1(6H, m), 2.75(3H, s), 3.31(2H, t, J= 2Hz), 3.45(4H, brs), 6.69(1H, m), 6.95(1H, dd, J=2 and 9Hz), 7.13(1H, d, J=2Hz), 7.38(1H, d, J=9Hz), 7.58(1H, d, J=2Hz). |
| 216 | 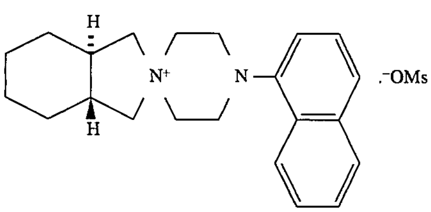 | Melting point: $^1$H-NMR (CDCl$_3$) δ: | 226–229° C. 8.11(1H, d, J=9Hz), 7.82– 7.86(1H, m), 7.63(1H, d, J= 8Hz), 7.36–7.53(3H, m), 7.15 (1H, d, J=7Hz), 3.9–4.1(6H, m), 3.4–3.5(6H, m), 2.78(3H, s), 1.2–2.2(10H, m). |
| 217 | 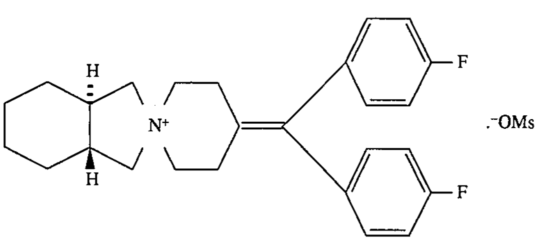 | Melting point: $^1$H-NMR (CDCl$_3$) δ: | 226–229° C. 6.98–7.15(8H, m), 4.0–4.1 (2H, m), 3.7–3.8(4H, m), 3.2– 3.3(2H, m), 2.76(3H, s), 2.6– 2.7(4H, m), 2.8–3.0(8H, m), 1.2–1.4(2H, m). |
| 218 | 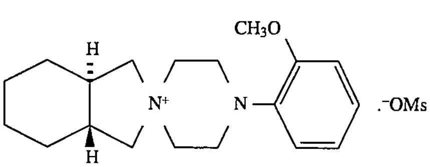 | Melting point: $^1$H-NMR (CDCl$_3$) δ: | 176–179° C. 6.8–7.1(4H, m), 3.9–4.0(2H, m), 3.7–3.8(7H, m), 3.35–3.45 (6H, m), 2.77(3H, s), 1.8–2.2 (6H, m), 1.3–1.4(4H, m). |

TABLE 7-continued

| Compound No. | Structure | Physical constant | |
|---|---|---|---|
| 219 | 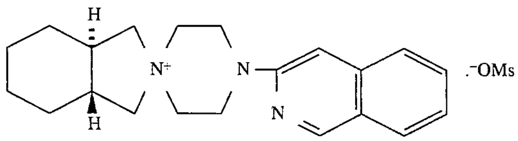 | Melting point:<br>¹H-NMR (CDCl₃) δ: | 215–216° C.<br>1.1–1.5(4H, m), 1.8–2.2(6H, m), 2.77(3H, s), 3.3–3.5(2H, m), 3.7–4.1(10H, m), 6.94(1H, s), 7.3–7.37(1H, m), 7.51–7.65(2H, m), 7.78(1H, d, J=8 Hz), 8.89(1H, s). |
| 220 | 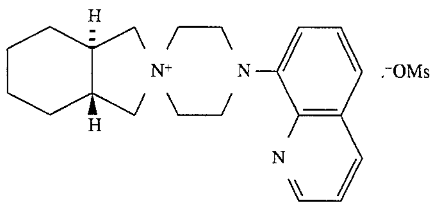 | Melting point:<br>¹H-NMR (CDCl₃) δ: | 112–113° C.<br>1.2–1.4(4H, m), 1.8–2.2(6H, m), 2.78(3H, s), 3.4–3.5(2H, m), 3.7–4.1(10H, m), 7.2–7.3(1H, m), 7.4–7.6(3H, m), 8.1–8.2(1H, m), 8.8–8.9(1H, m). |
| 221 | 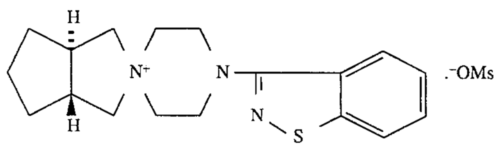 | Melting point:<br>¹H-NMR (CDCl₃) δ: | 194–195° C.<br>1.51(2H, quint, J=10Hz), 1.90(2H, m), 2.19–2.27(2H, m), 2.57(2H, m), 2.76(3H, s), 3.47(2H, t, J=11Hz), 3.92–4.08(10H, m), 7.38–7.53(2H, m), 7.83(1H, d, J=8Hz), 7.95(1H, d, J=8Hz). |
| 222 | 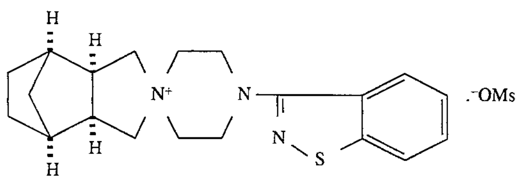 | Melting point:<br>¹H-NMR (CDCl₃) δ: | 224–227° C.<br>1.1–1.3(3H, m), 1.60(2H, m), 1.89(1H, d, J=15Hz), 2.25(2H, brs), 2.47(2H, m), 2.71(3H, s), 3.20(2H, m), 3.60–3.70(2H, m), 3.80–3.90(4H, m), 4.0–4.2(4H, m), 7.3–7.5(2H, m), 7.79(1H, d, J=8Hz), 7.96(1H, d, J=8Hz). |
| 223 | 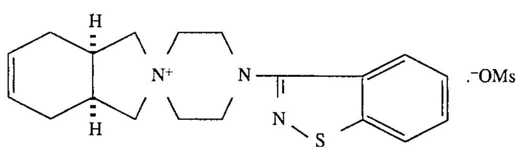 | ¹H-NMR (CDCl₃) δ: | 2.0–2.1(2H, m), 2.3–2.45(2H, m), 2.76(3H, s), 2.95–3.1(2H, m), 3.25–3.4(2H, m), 3.87(4H, brs), 3.96(4H, brs), 4.15–4.25(2H, m), 5.90(2H, brs), 7.38–7.53(2H, m), 7.82(1H, d, J=8 Hz), 7.99(1H, d, J=8Hz). |
| 224 | 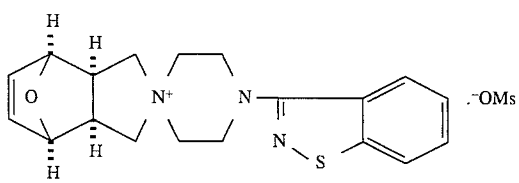 | ¹H-NMR (CDCl₃) δ: | 2.75(3H, s), 3.0–3.15(4H, m), 3.8–4.0(8H, m), 4.4–4.5(2H, m), 4.87(2H, s), 6.44(2H, s), 7.41–7.50(2H, m), 7.82(1H, d, J=8Hz), 7.98(1H, d, J=8Hz). |
| 225 | 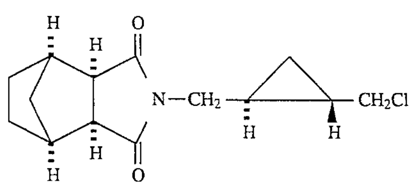 | ¹H-NMR (CDCl₃) δ: | 0.45(1H, m), 0.90(1H, m), 1.1–1.8(8H, m), 2.62(2H, m), 2.72(2H, brs), 3.20(2H, m), 3.50(2H, m). |
| 226 | 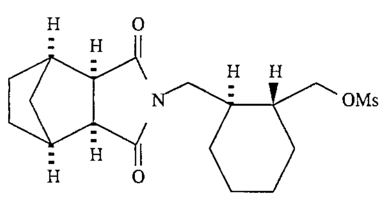 | ¹H-NMR (CDCl₃) δ: | 1.0–2.0(16H, m), 2.62(2H, brs), 2.70(2H, brs), 3.08(3H, s), 3.37(1H, dd, J=8Hz and 13Hz), 3.60(1H, dd, J=8Hz and 13Hz), 4.25–4.37(2H, m). |

TABLE 7-continued

| Compound No. | Structure | Physical constant | |
|---|---|---|---|
| 227 | [structure] | | |

Note: not isolated.

| 228 | [structure] | Melting point: | 216–218° C. |
| | | $^1$H-NMR (CDCl$_3$) δ: | 1.55–1.9(6H, m), 2.35–2.45 (2H, m), 2.75(3H, s), 2.95–3.05(2H, m), 3.35–3.5(2H, m), 3.75–4.0(8H, m), 4.1–4.2(2H, m), 7.38–7.53(2H, m), 7.82(1H, d, J=8Hz), 8.01(1H, d, J=8Hz). |

Reference Example 7

According to the methods as described in JP-A-63-83085, J. Med. Chem., 28, 761–769 (1985) or ibid., 32, 1024–1033 (1989), the compounds as shown in Table 8 are obtained.

TABLE 8

| Compound No. | Structure |
|---|---|
| 251 | [structure] |
| 252 | [structure] |
| 253 | [structure] |
| 254 | [structure] |

TABLE 8-continued

| Compound No. | Structure |
|---|---|
| 255 | [structure] |
| 256 | [structure] |
| 257 | [structure] |
| 258 | [structure] |
| 259 | [structure] |

TABLE 8-continued

| Compound No. | Structure |
|---|---|
| 260 | (cyclohexane-1,2-dicarboximide with two H₃C groups) |
| 261 | (norbornene dicarboximide) |
| 262 | (bicyclic dicarboximide) |
| 263 | (phthalimide) |
| 264 | (tetrahydrophthalimide) |
| 265 | (1-(2-pyrimidinyl)piperazine) |
| 266 | (piperidinyl-isoxazole with 4-F phenyl) |
| 267 | (piperidinyl ketone with 4-F phenyl) |
| 268 | (piperidinyl-indazole with F) |
| 269 | (piperidinyl-indole) |

Example 1- (a)

Production of Compound No. 101:—

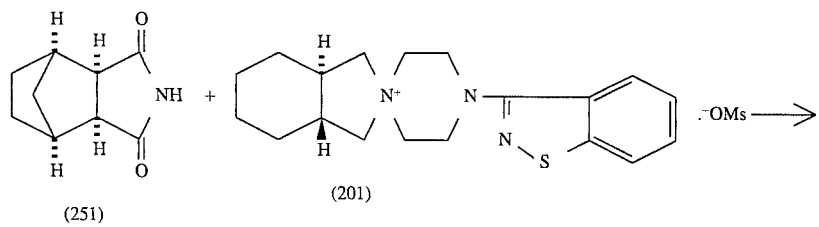

(251) + (201) .⁻OMs ⟶

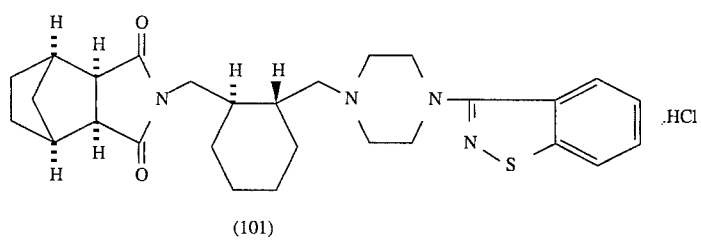

(101) .HCl

A mixture of the compound (201) (1.44 g; 3.4 mmol), bicyclo[2.2.1]heptane-2-exo-3-exo-dicarboximide (251) (0.84 g; 5.1 mmol), potassium carbonate (0.68 g; 5.0 mmol), dibenzo-18-crown-6-ether (4 mg; 0.01 mmol) and xylene (20 ml) is refluxed #or 16 hours, followed by removal of the solvent. The residue is chromatographed on a silica gel column and treated with hydrogen chloride-2-propanol to give the objective compound (Compound No. 101) in the form of hydrochloride. m.p., 215° to 217° C.

Example 1- (b)

A mixture of the compound No. 101 in the free form (145.0 g) and methanol (1350 ml) is heated at 60° C., and a solution of L-tartaric acid (44.4 g) in methanol (100 ml) is dropwise added thereto, and the resultant mixture is refluxed for 30 minutes. After allowing to cool to 20° to 30° C., the reaction mixture is stirred for 2 hours, and precipitated crystals are collected by filtration and dried under reduced pressure. The resulting crystals (103.5 g) are recrystallized from methanol two times to give a (+)-isomer of Compound No. 101 in the form of L-tartrate, i.e. Compound No. 102, (71.3 g). m.p., 129° C. $[\alpha]^{25}_D$=+18.2 (c=1.0, dimethylformamide (DMF))

Example 1-(c)

The mother liquor after collection of the first crystals by filtration in Example 1-(b) is concentrated under reduced pressure, followed by addition of dichloromethane (500 ml) and aqueous sodium bicarbonate (200 ml). The organic layer is washed with aqueous sodium bicarbonate and aqueous sodium chloride (500 ml) two times in order, dried and concentrated under reduced pressure. To the residue, methanol (3300 ml) and D-tartaric acid (20.2 g) are added, and the resultant mixture is stirred under reflux, followed by cooling. Stirring is continued at 20° to 30° C. for 2 hours, and precipitated crystals are collected and dried under reduced pressure to give crystals (88.0 g). The thus obtained crystals are recrystallized from methanol to give a (−)-isomer of Compound No. 101 in the form of D-tartrate, i.e. Compound No. 103, (67.5 g). m.p., 129° C. $[\alpha]_D^{25}$=−18.3 (c=1.0, DMF).

Example 1- (d)

A solution of Compound No. 102 (70.0 g) as obtained in Example 1-(b) in chloroform (500 ml) is washed with aqueous sodium bicarbonate (200 ml) two times and aqueous sodium chloride two times in order, dried and concentrated under reduced pressure. To the residue, acetone (270 ml) and 13.7% 2-propanol solution of hydrogen chloride (31.9 g) are added, and the mixture is stirred at 20° to 30° C. for 2 hours. Precipitated crystals are collected by filtration and dried under reduced pressure to give a (+)-isomer of Compound No. 101 in the form of hydrochloride, i.e. Compound No. 104, (55.9 g). m.p., 268° C. $[\alpha]^{25}_D$=+45.7° (c=1.0, methanol)

Example 1- (e)

Compound No. 103 as obtained in Example 1-(c) (65.0 g) is treated in the same manner as in Example 1-(d) to give a (−)-isomer of Compound No. 101 in the form of hydrochloride, i.e. Compound No. 105. m.p., 268° C. $[\alpha]^{25}_D$=−45.8 (c=1.0, methanol).

Example 2

Production of Compound No. 106:—

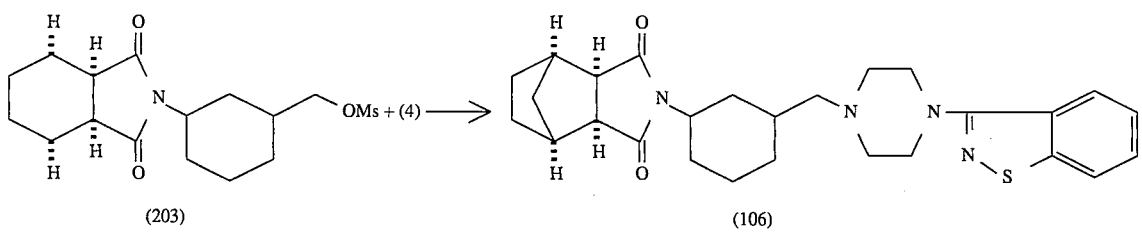

A solution of the compound (203) (90 mg; 0.25 mmol), sodium carbonate (90 rag; 0.85 mmol) and 3-(1-piperazinyl)-1,2-benzisothiazole (4) (180 mg; 0.82 mmol) in acetonitrile (5 ml) is refluxed for 30 hours. After removal of the solvent, chloroform is added to the reaction mixture. The resultant solution is washed with water, dried and concentrated. The residue is chromatographed on a silica gel column to give the objective compound (Compound No. 106).

$^1$H-NMR (CDCl$_3$) δ: 0.9–2.0 (14 H, m), 2.05–2.35 (3 H, m), 2.55 (2 H, s), 2.65 (4 H, brs), 2.75 (2 H, s), 3.55 (4 H, brs), 4.00 (1 H, m), 7.33–7.50 (2 H, m), 7.80 (1 H, d, J=8 Hz), 7.90 (1 H, d, J=8 Hz).

Example 3

Production of Compound No. 107:—

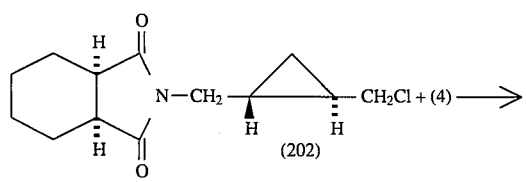

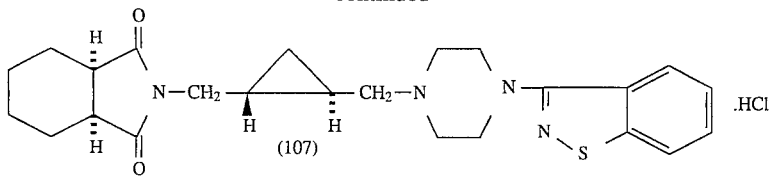

A mixture of the compound (202) (0.1 g; 0.39 mmol), 3-(1-piperazinyl)-1,2-benzisothiazole (4) (0.129 g; 0.58 mmol), potassium carbonate (0.1 g; 0.72 mmol), potassium iodide (0.1 g; 0.60 mmol) and acetonitrile (5 ml) is refluxed for 5.5 hours. The reaction mixture is concentrated under reduced pressure, and chloroform is added to the residue, which is washed with water, dried and concentrated under reduced pressure. The residue is chromatographed on a silica gel thin layer to give the objective compound (Compound No. 107) in the form of hydrochloride. m.p., 207° C.

Example 4

Production of Compound No. 108:— residue is chromatographed on a silica gel column and treated with hydrogen chloride-2-propanol to give the objective compound (Compound No. 108) in the form of hydrochloride. m.p., 208° to 210° C.

$^1$H-NMR (CDCl$_3$) δ: 1.08–2.1 (10 H, m), 2.2–2.68 (12 H, m), 3.5–3.6 (6 H, m), 7.30–7.48 (2 H, m), 7.80 (1 H, d, J=8.3 Hz), 7.90 (1 H, d, J=8.3 Hz).

Example 5

Production of Compound No. 109:—

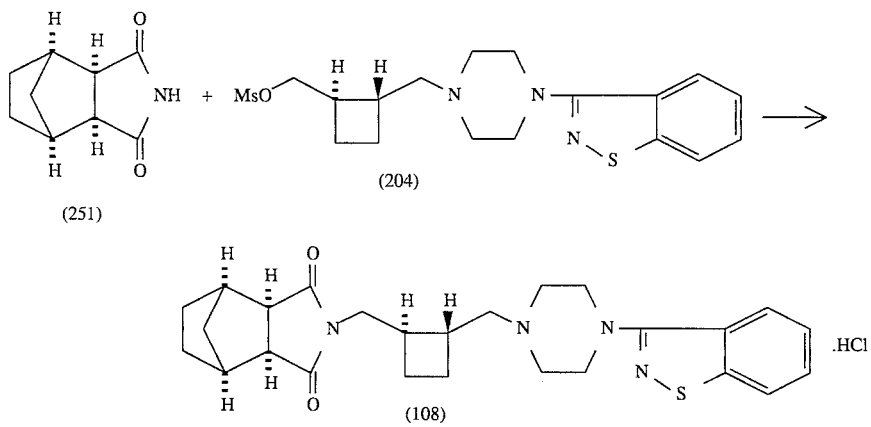

A solution of the compound (204) (1.18 g; 0.0030 mol), bicyclo[2.2.1]heptane-2-exo-3-exo-dicarboximide (251) (0.49 g); 0.0030 tool), potassium carbonate (0.41 g; 0.0030 mol) and dibenzo-18-crown-6-ether (10 mg) in xylene (30 ml) is refluxed for 20 hours. The reaction mixture is filtered, and the filtrate is concentrated under reduced pressure. The

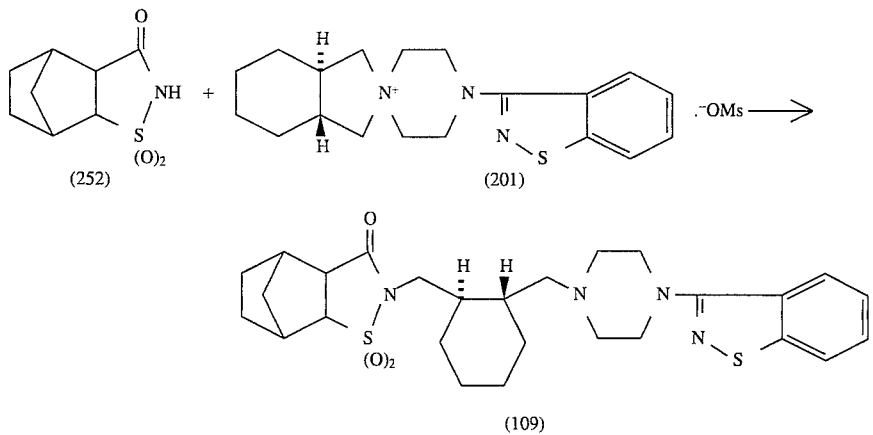

A mixture of the compound (201) (0.46 g; 0.0011 mol), the compound (252) (0.20 g; 0.00099 mol), potassium carbonate (0.14 g; 0.0011 mol), dibenzo-18-crown-6-ether (1 mg) and dimethylformamide (5 ml) is refluxed for 6 hours, followed by concentration under reduced pressure. The residue is chromatographed on a silica gel column to give the objective compound (Compound No. 109).

$^1$H-NMR (CDCl$_3$) δ: 0.95–1.9 (15 H, m), 2.1–2.3 (2 H, m), 2.5–2.7 (5 H, m), 2.9 (2 H, brs), 3.33 (0.5 H, dd, J=10 and 14.6 Hz), 3.42 (0.5 H, dd, J=10 and 14.2 Hz), 4.12 (0.5 H, dd, J=4.6 and 14.2 Hz), 4.2 (0.5 H, dd, J=4.6 and 14.6 Hz), 7.27–7.49 (2 H, m), 7.80 (1 H, d, J=8 Hz), 7.91 (1 H, d, J=8 Hz).

EI-MS m/e: 528.

Example 6

Production of Compound No. 110:—

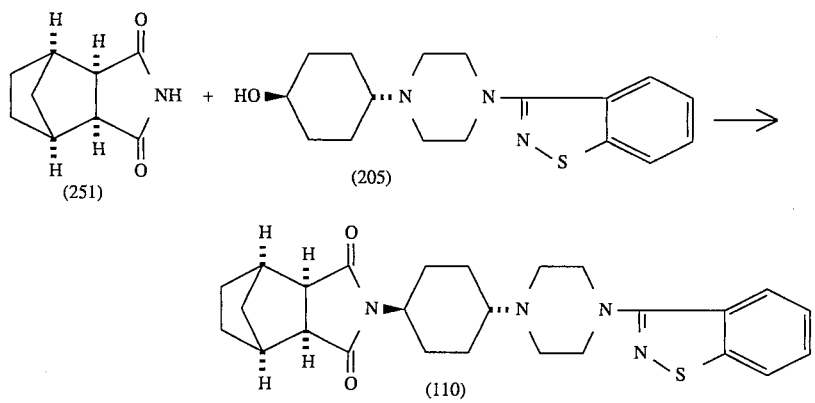

To a solution of the compound (205) (0.7 g; 2.2 mmol), bicyclo[2.2.1]heptane-2-exo-3-exo-dicarboximide (251) (0.73 g; 4.4 mmol) and triphenylphosphine (0.69 g; 2.6 mmol) in tetrahydrofuran (50 ml), a solution of diethyl azodicarboxylate (0.11 g; 2.6 mmol), in tetrahydrofuran (10 ml) is dropwise added at room temperature, followed by stirring at the same temperature for 3 hours. The reaction mixture is concentrated under reduced pressure, and the residue is chromatographed on a silica gel column to give the objective compound (Compound No. 110). m.p., 200° to 201° C.

$^1$H-NMR (CDCl$_3$) δ: 1.05–1.7 (10 H, m), 2.05–2.25 (2 H, m), 2.25–2.35 (1 H, m), 2.5–2.75 (10 H, m), 3.5–3.7 (4 H, m), 3.95–4.1 (1 H, m), 7.32–7.49 (2 H, m), 7.81 (1 H, d, J=8 Hz), 7.92 (1 H, d, J=8 Hz).

Example 7

Production of Compound No. 111:—

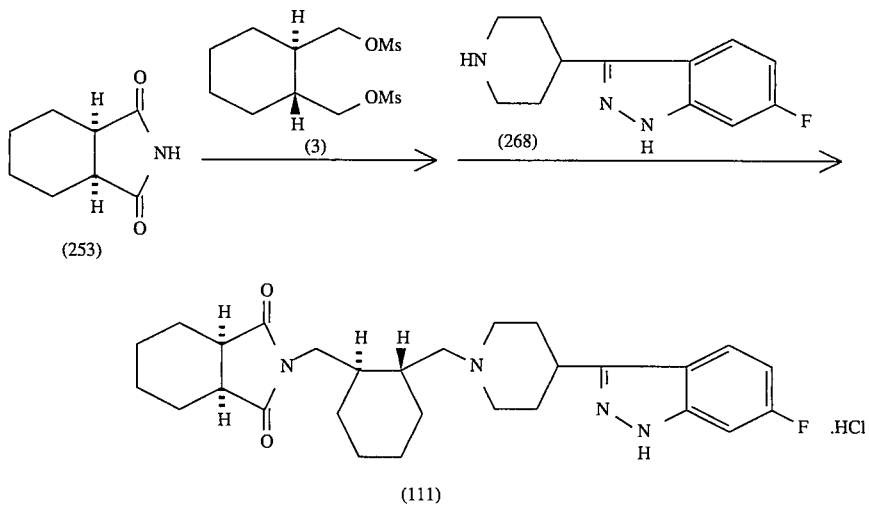

A mixture of cyclohexane-1,2-dicarboximide (253) (2 g; 0.013 mol), trans-1,2-his (methanesulfonyloxymethyl) cyclohexane (3) (5.88 g; 0.02 tool), potassium carbonate (1.8 g; 0.013 tool) and acetonitrile (50 ml) is refluxed for 2.5 hours. To the reaction mixture, there is added 6-fluoro-3-(4-piperidinyl)-1 H-indazole (268) (4.39 g; 0.02 tool), and the mixture is refluxed for additional 6 hours. The reaction mixture is filtered, and the filtrate is concentrated under reduced pressure. The residue is chromatographed on a silica gel column and treated with hydrogen chloride-2-propanol to give the objective compound (Compound No. 111) in the form of hydrochloride. m.p., 169° to 170° C.

$^1$H-NMR (CDCl$_3$) δ: 1.0–2.2 (25 H, m), 2.5–2.6 (1 H, m), 2.8–2.9 (2 H, m), 2.9–3.1 (3 H, m), 3.2–3.4 (1 H, m), 3.96 (1 H, dd, J=4 and 13 Hz), 6.85–6.93 (1 H, m), 7.07 (1 H, dd, J=2 and 9 Hz), 7.71 (1 H, dd, J=5 and 9 Hz), 9.78 (1 H, brs).

Examples 8 to 72

In the same manner as in Examples 1 to 7, the compounds as shown in Table 9 are obtained. The physical constants of these compounds are given in Table 10.

TABLE 9

| Example No. | Starting Compound No. | Objective Compound No. | Structure |
|---|---|---|---|
| 8 | 253 + 201 | 112 | 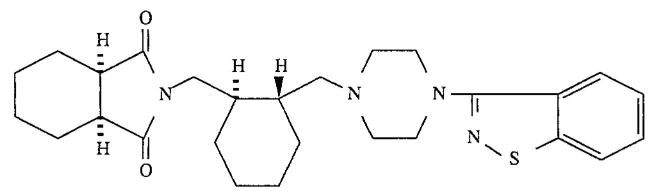 |
| 9 | 253 + 206 | 113 | 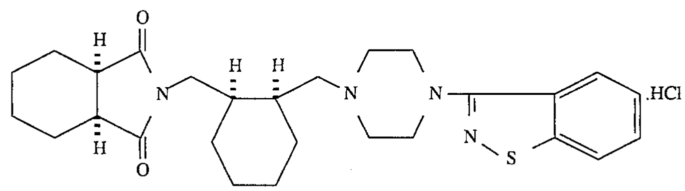 |
| 10 | 251 + 208 | 114 | 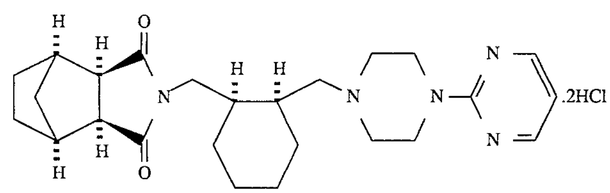 |
| 11 | 254 + 201 | 115 | 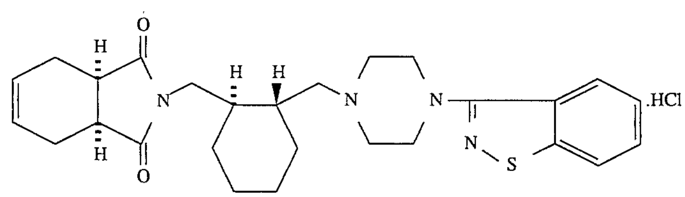 |
| 12 | 255 + 201 | 116 | 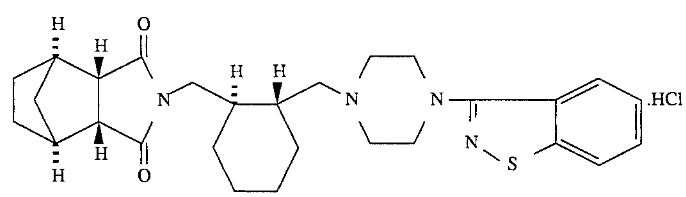 |
| 13 | 256 + 201 | 117 | 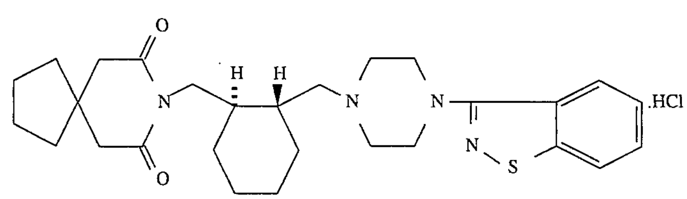 |

TABLE 9-continued

| Example No. | Starting Compound No. | Objective Compound No. | Structure |
|---|---|---|---|
| 14 | 257 + 201 | 118 | 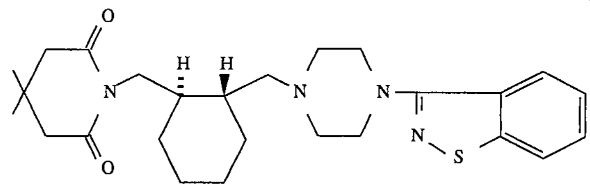 |
| 15 | 258 + 201 | 119 | 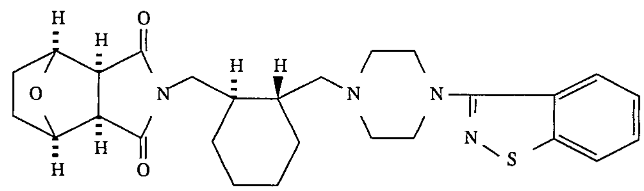 |
| 16 | 259 + 201 | 120 | 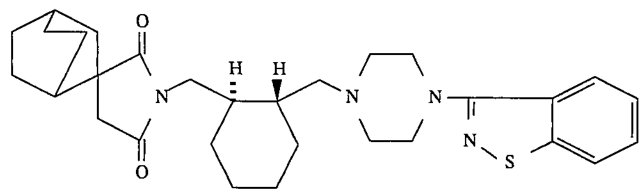 |
| 17 | 260 + 201 | 121 | 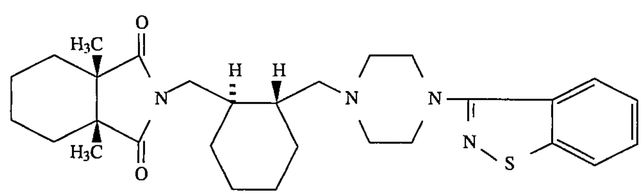 |
| 18 | 261 + 201 | 122 | 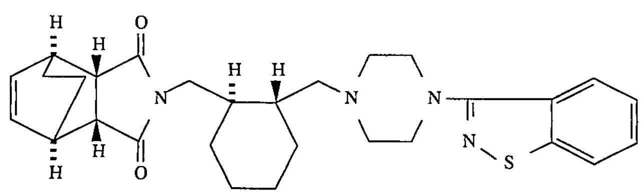 |
| 19 | 262 + 201 | 123 | 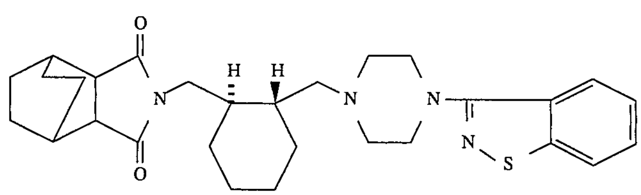 |
| 20 | 263 + 201 | 124 | 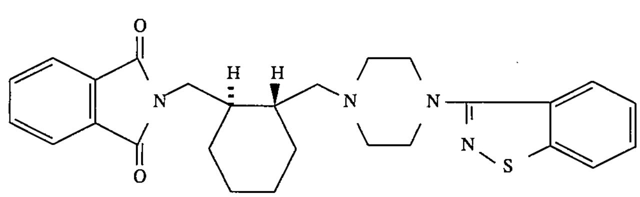 |
| 21 | 264 + 201 | 125 | 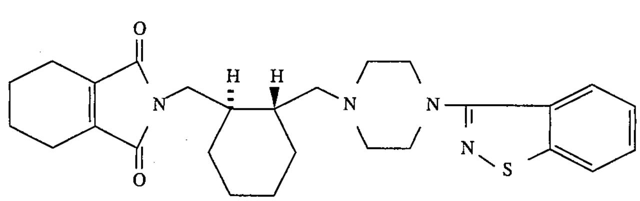 |

TABLE 9-continued

| Example No. | Starting Compound No. | Objective Compound No. | Structure |
|---|---|---|---|
| 22 | 251 + 206 | 126 | (structure) .HCl |
| 23 | 251 + 210 | 127 | (structure) .HCl |
| 24 | 253 + 210 | 128 | (structure) .HCl |
| 25 | 251 + 211 | 129 | (structure) |
| 26 | 253 + 211 | 130 | (structure) .HCl |
| 27 | 251 + 212 | 132 | (structure) |
| 28 | 253 + 212 | 132 | (structure) |
| 29 | 251 + 213 | 133 | (structure) |

TABLE 9-continued

| Example No. | Starting Compound No. | Objective Compound No. | Structure |
|---|---|---|---|
| 30 | 253 + 213 | 134 | 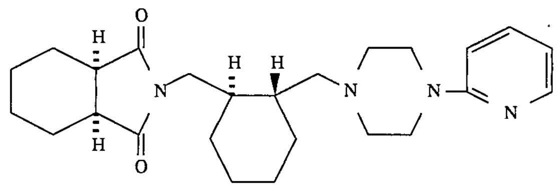 |
| 31 | 251 + 207 | 135 | 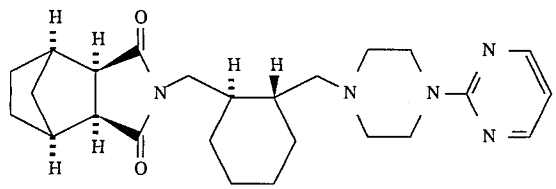 |
| 32 | 253 + 207 | 136 | 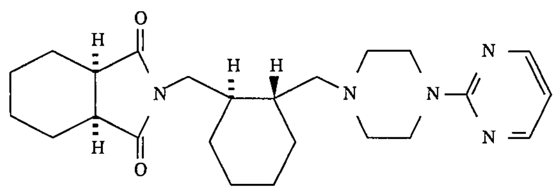 |
| 33 | 251 + 214 | 137 | 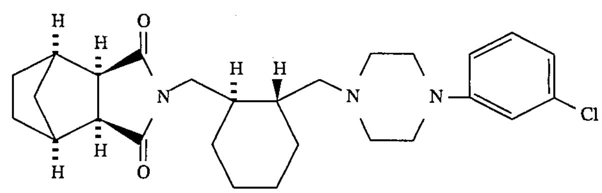 |
| 34 | 253 + 214 | 138 | 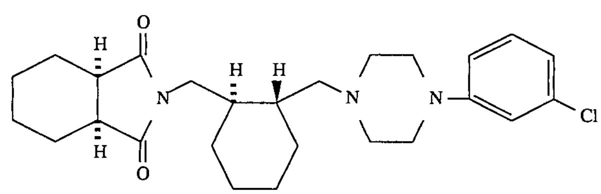 |
| 35 | 251 + 215 | 139 | 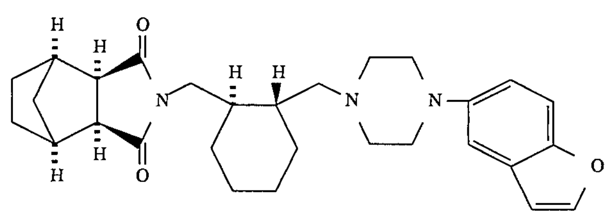 |
| 36 | 253 + 215 | 140 | 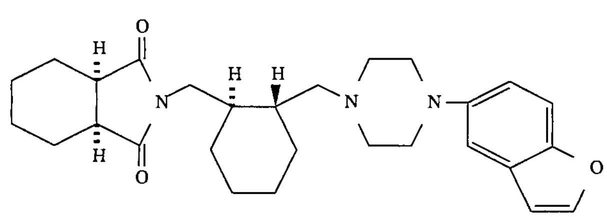 |

TABLE 9-continued

| Example No. | Starting Compound No. | Objective Compound No. | Structure |
|---|---|---|---|
| 37 | 251 + 216 | 141 | 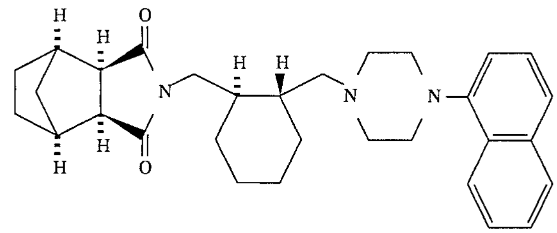 |
| 38 | 253 + 216 | 142 | 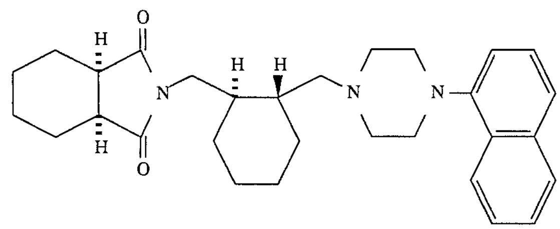 |
| 39 | 251 + 217 | 143 | 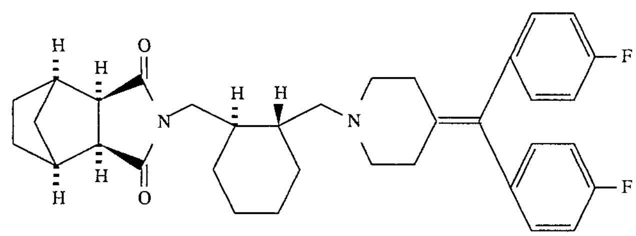 |
| 40 | 253 + 217 | 144 | 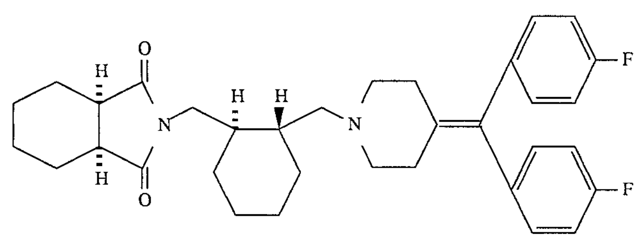 |
| 41 | 251 + 218 | 145 | 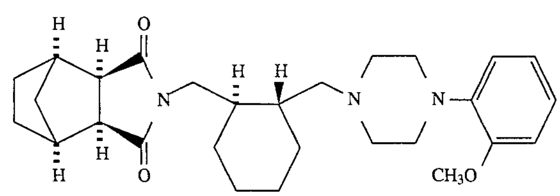 |
| 42 | 253 + 218 | 146 | 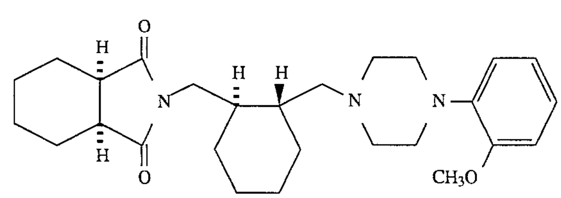 |
| 43 | 251 + 219 | 147 | 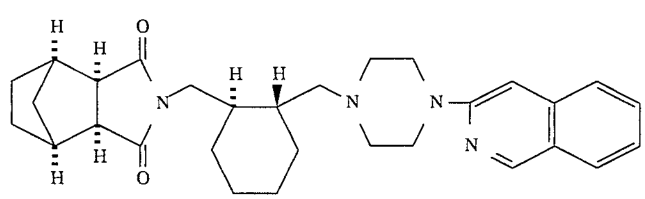 |

TABLE 9-continued

| Example No. | Starting Compound No. | Objective Compound No. | Structure |
|---|---|---|---|
| 44 | 253 + 219 | 148 | 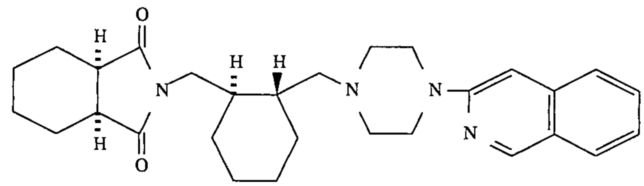 |
| 45 | 251 + 220 | 149 | .2HCl |
| 46 | 253 + 220 | 150 | 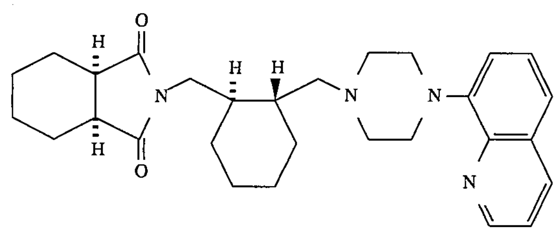 |
| 47 | 251 + 221 | 151 | 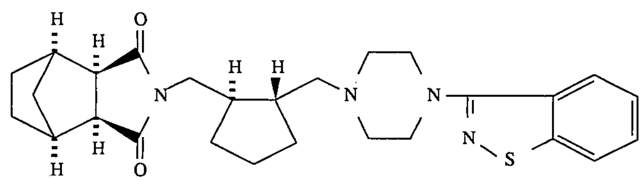 |
| 48 | 253 + 221 | 152 | 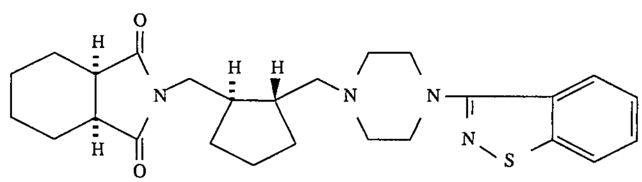 |
| 49 | 251 + 222 | 153 | 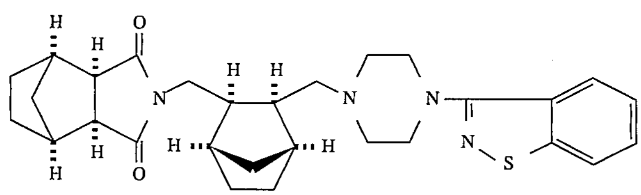 |
| 50 | 253 + 222 | 154 | 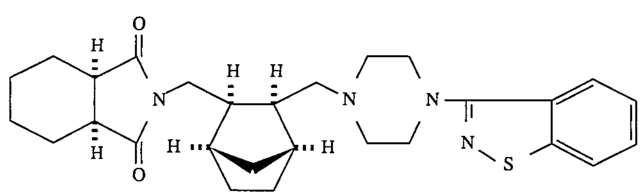 |

TABLE 9-continued

| Example No. | Starting Compound No. | Objective Compound No. | Structure |
|---|---|---|---|
| 51 | 251 + 227 | 155 | 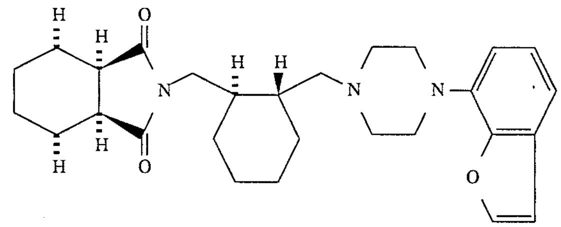 |
| 52 | 253 + 227 | 156 | 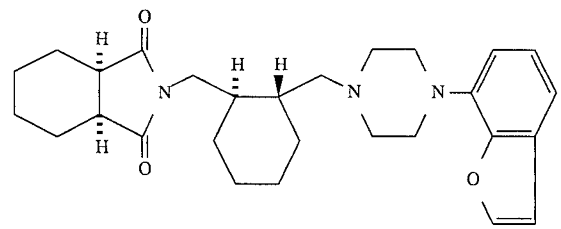 |
| 53 | 209 + 4 | 157 | 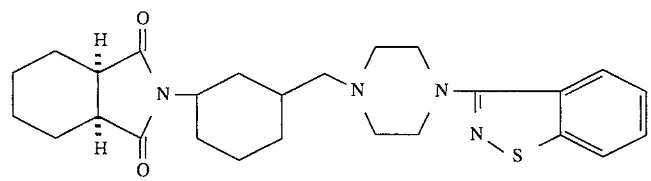 |
| 54 | 209 + 265 | 158 | 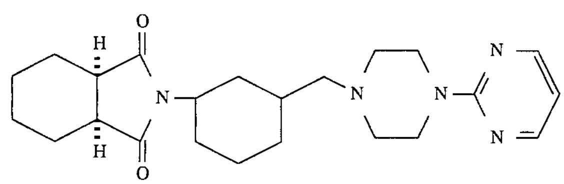 |
| 55 | 202 + 265 | 159 | 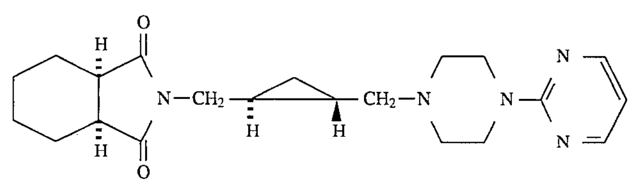 |
| 56 | 202 + 266 | 160 | 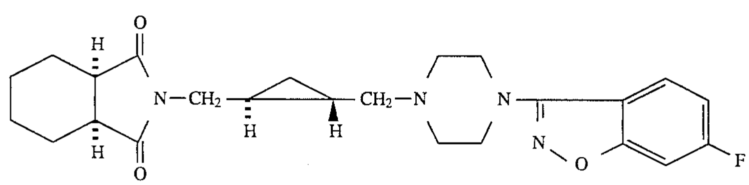 |
| 57 | 202 + 267 | 161 | 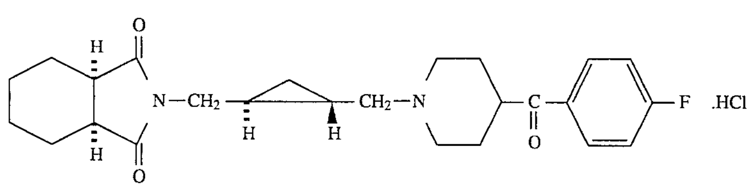 |
| 58 | 225 + 4 | 162 | 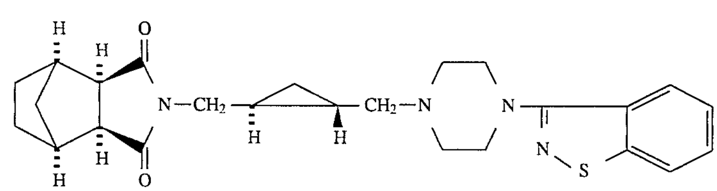 |

TABLE 9-continued
| Example No. | Starting Compound No. | Objective Compound No. | Structure |
|---|---|---|---|
| 59 | 225 + 265 | 163 | 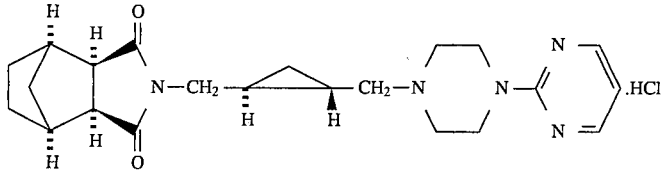 |
| 60 | 253 + 204 | 164 | 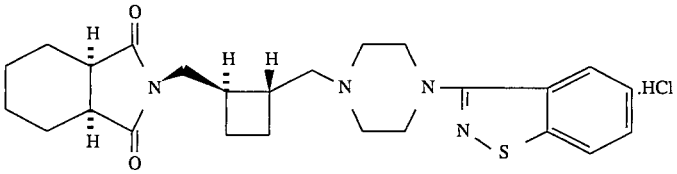 |
| 61 | 253 + 205 | 165 | 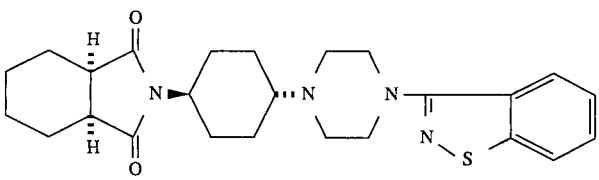 |
| 62 | 251 + 3 + 268 | 166 | 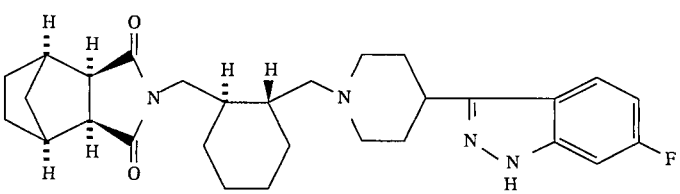 |
| 63 | 253 + 3 + 269 | 167 | 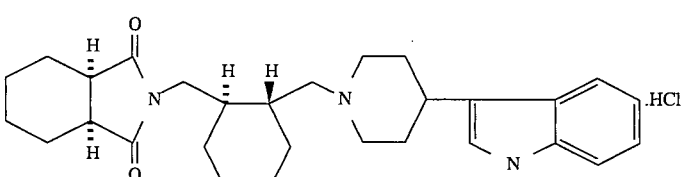 |
| 64 | 251 + 3 + 269 | 168 | 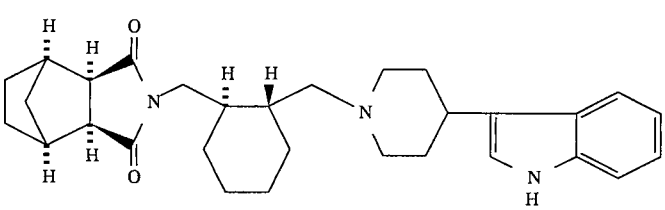 |
| 65 | 253 + 3 + 267 | 169 | 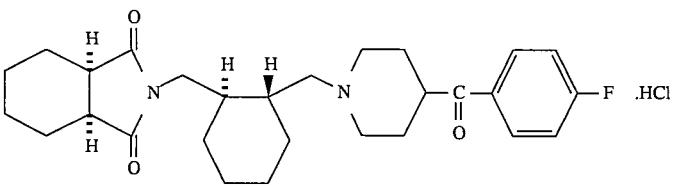 |
| 66 | 251 + 3 + 267 | 170 | 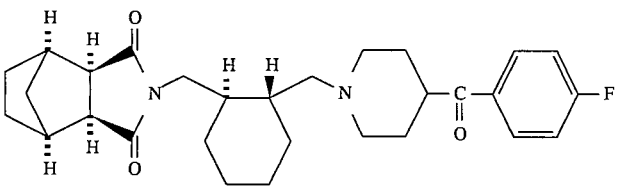 | ns
TABLE 9-continued

| Example No. | Starting Compound No. | Objective Compound No. | Structure |
|---|---|---|---|
| 67 | 251 + 224 | 171 | 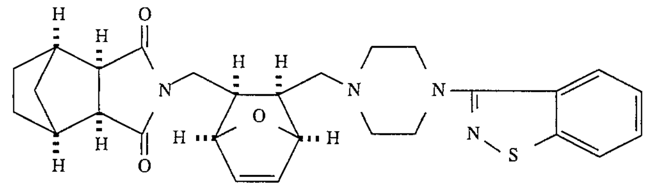 |
| 68 | 253 + 224 | 172 | 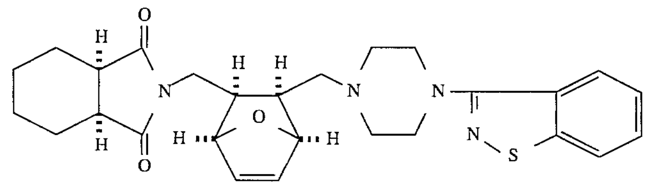 |
| 69 | 251 + 223 | 173 | 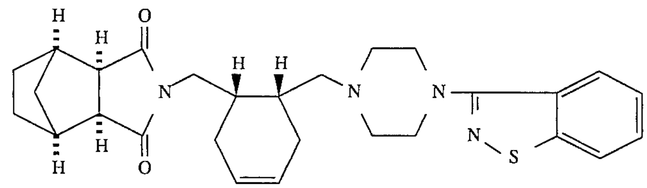 |
| 70 | 253 + 223 | 174 | 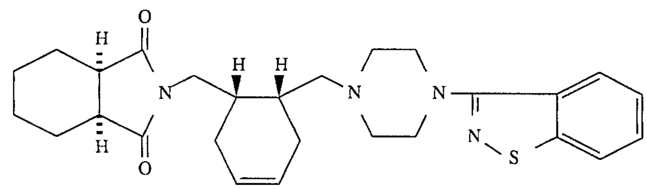 |
| 71 | 253 + 228 | 175 | 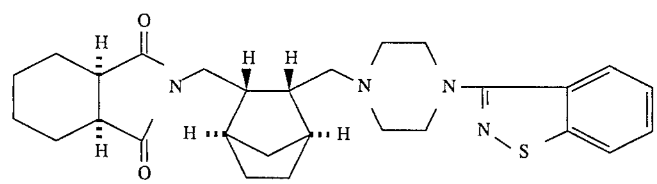 |
| 72 | 251 + 228 | 176 | 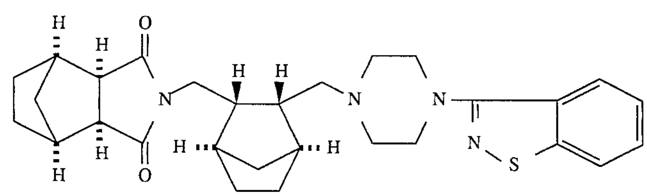 |

TABLE 10

| Example No. | Compound No. | Melting point (°C.) | $^1$H-NMR (CDCl$_3$) δ (free form) |
|---|---|---|---|
| 8 | 112 | 140 | |
| 9 | 113 | 145–150 | |
| 10 | 114 | 230 | |
| 11 | 115 | 107–110 | 0.92–1.9(10H, m), 2.19–2.26(3H, m), 2.58–2.64(7H, m), 3.07(2H, t, J=3Hz), 3.32(1H, dd, J=13 and 10 Hz), 3.52(4H, t, J=4Hz), 3.91(1H, dd, J=13 and 4Hz), 5.90(2H, t, J=3Hz), 7.32–7.49(2H, m), 7.78–7.92 (2H, m). |
| 12 | 116 | 231–233 | 1.03–1.91(16H, m), 2.24(1H, dd, J=12 and 7Hz), 2.60–2.76(7H, m), 3.07(2H, t, J=2Hz), 3.32(1H, dd, J=13 and 10Hz), 3.52(4H, t, J=5Hz), 3.95(2H, dd, J=13 and 4Hz), 7.32–7.49 (2H, m), 7.78–7.92(2H, m). |
| 13 | 117 | 212–214 | 0.96–1.9(18H, m), 2.24(1H, dd, J=12 and 7Hz), 2.53– |

TABLE 10-continued

| Example No. | Compound No. | Melting point (°C.) | $^1$H-NMR (CDCl$_3$) δ (free form) |
|---|---|---|---|
| 14 | 118 | 124–125 | 2.65(9H, m), 3.53(4H, t, J=5Hz), 3.77(1H, dd, J=13 and 10Hz), 4.07(1H, dd, J=13 and 4Hz), 7.32–7.49(2H, m), 7.78–7.92(2H, m). 0.85–1.9(16H, m), 2.23(1H, dd, J=12 and 7Hz), 2.44–2.66(9H, m), 3.52(4H, t, J=5Hz), 3.78(1H, dd, J=13 and 10Hz), 4.10(1H, dd, J=13 and 4Hz), 7.32–7.49(2H, m), 7.78–7.92(2H, m). |
| 15 | 119 | 217–219 | 0.9–1.9(14H, m), 2.24(1H, m), 2.63(5H, brs), 2.86(2H, s), 3.32(1H, dd, J=13 and 10Hz), 3.52(4H, brs), 3.90 (1H, brd, J=9Hz), 4.87 (2H, s), 7.32–7.48(2H, m), 7.78–7.92(2H, m). |
| 16 | 120 | 118–120 | 1.9–2.0(20H, m), 2.1–2.3 (3H, m), 2.4–2.5(1H, m), 2.5–2.8(5H, m), 2.96(1H, d, J=18Hz), 3.32(1H, dd, J=10 and 13Hz), 3.5–3.6(4H, m), 3.88–3.94(1H, m), 7.32–7.49(2H, m), 7.79–7.92(2H, m). |
| 17 | 121 | 173–174 | 1.15(6H, s), 1.0–2.0(18H, m), 2.2–2.3(1H, m), 2.5–2.7(5H, m), 3.3(1H, t, J=11Hz), 3.5–3.6(4H, m), 3.8 (1H, d, J=13Hz), 7.33–7.49(2H, m), 7.79–7.93(2H, m). |
| 18 | 122 | 146–147 | 0.8–1.8(14H, m), 1.8–1.9 (1H, m), 2.2–2.3(1H, m), 2.5–2.7(4H, m), 2.85(2H, m), 3.1–3.2(2H, m), 3.25 (1H, dd, J=10 and 13Hz), 3.45–3.6(4H, m), 3.85(1H, dd, J=3 and 13Hz), 6.14–6.2(2H, m), 7.33–7.49(2H, m), 7.79–7.92(2H, m). |
| 19 | 123 | 157–158 | 1.0–1.8(17H, m), 1.9–2.0 (1H, m), 2.1–2.2(2H, m), 2.25(1H, dd, J=7 and 13Hz), 2.6–2.7(5H, m), 2.8(2H, s), 3.38(1H, dd, J=10 and 13Hz), 3.5–3.6(4H, m), 4.0 (1H, dd, J=3 and 13Hz), 7.32–7.49(2H, m), 7.79–7.93(2H, m). |
| 20 | 124 | 160–162 | 1.0–2.0(10H, m), 2.29(1H, dd, J=13 and 7Hz), 3.48–3.54(5H, m), 4.16(1H, dd, J=13 and 4Hz), 7.33–7.49 (2H, m), 7.70–7.94(6H, m). |
| 21 | 125 | 183–184 | 0.8–1.8(13H, m), 1.9–2.0 (1H, m), 2.2–2.4(5H, m), 2.6–2.7(4H, m), 3.3(1H, dd, J=10 and 13Hz), 3.5–3.6(4H, m), 3.89–3.93(1H, m), 7.32–7.49(2H, m), 7.79–7.93(2H, m). |
| 22 | 126 | 235–236 | 1.1–1.7(12H, m), 1.8–2.1 (4H, m), 2.3–2.75(10H, m), 3.35–3.6(6H, m), 7.32–7.49 (2H, m), 7.80(1H, d, J=8Hz), 7.91(1H, d, J=8Hz). |
| 23 | 127 | 107–110 | 0.8–2.0(22H, m), 2.07(1H, dd, J=7 and 13Hz), 2.46(1H, dd, J=6 and 13Hz), 2.58(2H, s), 2.67(2H, brs), 2.75–3.0 (3H, m), 3.25(1H, dd, J=10 and 13Hz), 3.84(1H, dd, J=4 and 13Hz), 6.9–7.1(2H, m), 7.3–7.5(2H, m). |
| 24 | 128 | 169–171 | 0.8–2.0(22H, m), 2.07(1H, dd, J=7 and 12Hz), 2.45(1H, dd, J=7 and 12Hz), 2.7–3.0 (7H, m), 3.26(1H, dd, J=10 and 13Hz), 3.84(1H, dd, J=4 and 14Hz), 6.95–7.02(2H, m), 7.36–7.43(2H, m). |
| 25 | 129 | 115–117 | 0.8–2.0(20H, m), 2.0–2.3 (3H, m), 2.51(1H, dd, J=6 and 12Hz), 2.59(2H, s), 2.70 (4H, brs), 3.28(1H, dd, J=10 and 13Hz), 3.88(1H, dd, J=4 and 13Hz), 4.17(1H, m), 6.8–7.0(4H, m). |
| 26 | 130 | 145–148 | 0.8–2.0(22H, m), 2.0–2.3 (3H, m), 2.51(1H, dd, J=6 and 12Hz), 2.6–2.9(4H, m), 3.31(1H, dd, J=10 and 13Hz), 3.89(1H, dd, J=4 and 13Hz), 4.17(1H, m), 6.75–7.0 (4H, m). |
| 27 | 131 | 121–123 | 0.9–1.8(15H, m), 1.8–1.95 (1H, m), 1.95–2.15(6H, m), 2.17(1H, dd, J=7 and 13Hz), 2.56(1H, dd, J=6 and 12Hz), 2.60(2H, s), 2.70(2H, s), 2.9–3.1(3H, m), 3.30(1H, dd, J=10 and 13Hz), 3.91 (1H, dd, J=4 and 13Hz), 7.04 (1H, dt, J=2 and 9Hz), 7.23 (1H, dd, J=2 and 9Hz), 7.68 (1H, dd, J=5 and 8Hz). |
| 28 | 132 | 104–107 | 0.9–2.0(18H, m), 2.0–2.2 (6H, m), 2.17(1H, dd, J=7 and 13Hz), 2.56(1H, dd, J=6 and 13Hz), 2.8–2.9(2H, m), 2.95–3.1(3H, m), 3.33 (1H, dd, J=10 and 14Hz), 3.92(1H, dd, J=4 and 13Hz), 7.05(1H, dt, J=2 and 9Hz), 7.23(1H, dd, J=3 and 9Hz), 7.68(1H, m). |
| 29 | 133 | 161–163 | 0.9–1.75(15H, m), 1.8–1.95 (1H, m), 2.18(1H, dd, J=7 and 13Hz), 2.4–2.65(7H, m), 2.69(1H, brs), 3.29(1H, dd, J=10 and 13Hz), 3.50(4H, t, 5Hz), 3.90(1H, dd, J=4 and 13Hz), 6.55–6.7(2H, m), 7.46(1H, m), 8.17(1H, m). |
| 30 | 134 | 106–108.5 | 0.9–2.0(18H, m), 2.18(1H, dd, J=7 and 13Hz), 2.4–2.6 (5H, m), 2.75–2.9(2H, m), 3.32(1H, dd, J=10 and 13Hz), 3.50(4H, t, J=5Hz), 3.90(1H, dd, J=4 and 13Hz), 6.55–6.7(2H, m), 7.45(1H, m), 8.17(1H, m). |
| 31 | 135 | 145–147 | 0.9–1.75(15H, m), 1.8–1.95 (1H, m), 2.16(1H, dd, J=7 and 13Hz), 2.35–2.65(7H, m), 2.70(2H, brs), 3.30(1H, dd, J=10 and 13Hz), 3.78 (4H, t, J=5Hz), 3.88(1H, dd, J=4 and 13Hz), 6.46(1H, t, J=5Hz), 8.29(2H, d, J=5Hz). |
| 32 | 136 | 92–94 | 0.9–2.0(18H, m), 2.17(1H, dd, J=7 and 12Hz), 2.35–2.55(4H, m), 2.54(1H, dd, J=6 and 13Hz), 2.75–2.9 (2H, m), 3.32(1H, dd, J=10 and 13Hz), 3.79(4H, t, J=5Hz), 3.89(1H, dd, J=4 and 14Hz), 6.44(1H, t, J=5Hz), 8.29(2H, d, J=5Hz). |

TABLE 10-continued

| Example No. | Compound No. | Melting point (°C.) | ¹H-NMR (CDCl₃) δ (free form) |
|---|---|---|---|
| 33 | 137 | 134–136.5 | 0.9–1.8(15H, m), 1.8–1.95 (1H, m), 2.18(1H, dd, J=7 and 12Hz), 2.45–2.65 (7H, m), 2.70(2H, brs), 3.16(4H, m), 3.29(2H, dd, J=10 and 13Hz), 3.89(1H, dd, J=4 and 13Hz), 6.7–6.9(3H, m), 7.15(1H, m). |
| 34 | 138 | 89–91.5 | 0.9–2.0(18H, m), 2.19(1H, dd, J=7 and 13Hz), 2.45–2.65(5H, m), 2.84(2H, m), 3.16(4H, m), 3.32(1H, dd, J=10 and 13Hz), 3.9(1H, dd, J=7 and 13Hz), 6.7–6.9 (3H, m), 7.15(1H, m). |
| 35 | 139 | 185–186 | 0.9–1.75(15H, m), 1.75–1.95(1H, m), 2.21(1H, dd, J=7 and 13Hz), 2.5–2.75(9H, m), 3.14(4H, m), 3.30(1H, dd, J=10 and 13Hz), 3.91(1H, dd, J=4 and 13Hz), 6.68(1H, m), 6.99(1H, dd, J=2 and 9Hz), 7.08(1H, d, J=2Hz), 7.38(1H, d, J=9Hz), 7.56 (1H, d, J=2Hz). |
| 36 | 140 | 147.5–149 | 0.9–2.0(18H, m), 2.22(1H, dd, J=7 and 13Hz), 2.5–2.7(5H, m), 2.84(2H, m), 3.14 (4H, m), 3.33(1H, dd, J=10 and 13Hz), 3.92(1H, dd, J=4 and 13Hz), 6.68(1H, m), 6.99 (1H, dd, J=3 and 9Hz), 7.09 (1H, d, J=2Hz), 7.38(1H, d, J=9Hz), 7.56(1H, d, J=2Hz). |
| 37 | 141 | 106–107 | 1.0–1.8(16H, m), 1.9–2.0 (1H, m), 2.27(1H, dd, J=6 and 13Hz), 2.5–2.8(8H, m), 3.0–3.2(4H, m), 3.3(1H, dd, J=10 and 13Hz), 3.94(1H, dd, J=4 and 13Hz), 7.07(1H, d, J=7Hz), 7.36–7.55(4H, m), 7.8–7.9(1H, m), 8.18–8.21(1H, m). |
| 38 | 142 | 100–101.5 | 1.0–2.0(19H, m), 2.26(1H, dd, J=7 and 12Hz), 2.6–2.9 (6H, m), 3.0–3.2(4H, m), 3.36(1H, dd, J=10 and 13Hz), 3.95(1H, dd, J=4 and 13Hz), 7.07(1H, d, J=7Hz), 7.36–7.55(4H, m), 7.8–7.83 (1H, m), 8.18–8.21(1H, m). |
| 39 | 143 | 106–107 | 1.0–1.7(14H, m), 1.8–1.9 (1H, m), 2.12(1H, dd, J=7 and 13Hz), 2.3–2.6(10H, m), 2.59(2H, s), 2.69(2H, s), 3.29(1H, dd, J=10 and 13Hz), 3.86(1H, dd, J=3 and 13Hz), 6.9–7.1(8H, m). |
| 40 | 144 | 100–101.5 | 1.0–2.0(18H, m), 2.13(1H, dd, J=7 and 13Hz), 2.3–2.6 (9H, m), 2.8–2.9(2H, m), 3.31(1H, dd, J=4 and 10Hz), 3.87(1H, dd, J=4 and 13Hz), 6.93–7.07(8H, m). |
| 41 | 145 | 79–80 | 0.9–1.7(16H, m), 1.8–1.9 (1H, m), 2.21–2.29(1H, m), 2.5–2.75(8H, m), 2.9–3.1 (4H, m), 3.2–3.3(1H, m), 3.86(3H, s), 3.9–4.0(1H, m), 6.8–7.0(4H, m). |
| 42 | 146 | 78–79 | 0.9–2.0(18H, m), 2.21(1H, dd, J=12 and 7Hz), 2.5–2.6(5H, m), 2.7–2.8(2H, m), 2.9–3.1(4H, m), 3.32 (1H, dd, J=13 and 10Hz), 3.86(3H, s), 3.9–4.0(1H, m), 6.8–7.0(4H, m). |
| 43 | 147 | 187–188 | 1.0–1.75(15H, m), 1.8–2.0 (1H, m), 2.21(1H, dd, J=12 and 7Hz), 2.5–2.8(9H, m), 3.31(1H, dd, J=13 and 10Hz), 3.45–3.65(4H, m), 3.92 (1H, dd, J=13 and 4Hz), 6.75 (1H, s), 7.22–7.28(1H, m), 7.46–7.59(2H, m), 7.77(1H, d, J=8Hz), 8.93(1H, s). |
| 44 | 148 | 139–140 | 0.9–2.0(18H, m), 2.2(1H, dd, J=12 and 7Hz), 2.5–2.7 (5H, m), 2.8–2.95(2H, m), 3.3(1H, dd, J=13 and 10Hz), 3.45–3.65(4H, m), 3.93(1H, dd, J=9 and 4Hz), 6.75(1H, s), 7.22–7.28(1H, m), 7.46–7.6(2H, m), 7.78(1H, d, J=8Hz), 8.93(1H, s). |
| 45 | 149 | 268–270 | 1.0–2.0(16H, m), 2.27(1H, dd, J=12 and 7Hz), 2.6–2.9(9H, m), 3.3–3.5(5H, m), 3.94(1H, dd, J=13 and 4Hz), 7.11–7.15(1H, m), 7.3–7.5 (3H, m), 8.1(1H, d, J=8Hz), 8.87–8.89(1H, m). |
| 46 | 150 | 108–109 | 1.0–2.0(18H, m), 2.28(1H, dd, J=7 and 12Hz), 2.6–2.9 (7H, m), 3.3–3.5(5H, m), 3.95(1H, dd, J=13.5 and 4Hz), 7.11–7.15(1H, m), 7.34–7.47(3H, m), 8.1(1H, dd, J=8 and 2Hz), 8.87(1H, dd, J=4 and 2Hz). |
| 47 | 151 | 94–97 | 1.1–2.0(14H, m), 2.3–2.4 (2H, m), 2.5–2.71(8H, m), 3.42(1H, dd, J=13 and 9Hz), 3.54(4H, t, J=5Hz), 3.35 (1H, dd, J=5 and 13Hz), 7.32–7.49(2H, m), 7.81(1H, d, J=8Hz), 7.91(1H, d, J=8Hz). |
| 48 | 152 | 91–93 | 1.28–2.1(16H, m), 2.35(2H, m), 2.6–2.71(4H, m), 2.8–2.9(2H, m), 3.44(1H, dd, J=13 and 9Hz), 3.54(4H, t, J=5Hz), 3.66(1H, dd, J=13 and 6Hz), 7.32–7.49(2H, m), 7.78–7.93(2H, m). |
| 49 | 153 | 195–197 | 1.0–1.75(13H, m), 1.8–2.05 (3H, m), 2.15(1H, brs), 2.2–2.5(2H, m), 2.5–2.8(7H, m), 3.3–3.65(5H, m), 3.83(1H, dd, J=3 and 13Hz), 7.30–7.50(2H, m), 7.8(1H, d, J=8Hz), 7.91(1H, d, J=8Hz). |
| 50 | 154 | 164–167 | 1.0–1.25(3H, m), 1.3–2.1 (14H, m), 2.16(1H, brs), 2.2–2.45(2H, m), 2.55–2.75 (4H, m), 2.75–2.95(2H, m), 3.35–3.65(5H, m), 3.84(1H, dd, J=4 and 13Hz), 7.3–7.5 (2H, m), 7.8(1H, d, J=8Hz), 7.91(1H, d, J=8Hz). |
| 51 | 155 | 136–138 | 0.9–1.75(15H, m), 1.8–1.95 (1H, m), 2.23(1H, dd, J=7 and 12Hz), 2.5–2.8(9H, m), 3.2–3.4(5H, m), 3.92(1H, dd, J=4 and 13Hz), 6.7–6.8 (2H, m), 7.05–7.25(2H, m), 7.60(1H, d, J=2Hz). |
| 52 | 156 | 120–123 | 0.9–2.0(18H, m), 2.24(1H, dd, J=7 and 13Hz), 2.5–2.75(5H, m), 2.75–2.95(2H, m), 3.2–3.4(5H, m), 3.93 |

TABLE 10-continued

| Example No. | Compound No. | Melting point (°C.) | 1H-NMR (CDCl3) δ (free form) |
|---|---|---|---|
| 53 | 157 | | (1H, dd, J=4 and 13Hz), 6.7–6.8(2H, m), 7.05–7.25 (2H, m), 7.60(1H, d, J=2Hz). 1.0(1H, m), 1.3–1.9(15H, m), 2.10(1H, m), 2.30(2H, brs), 2.80(2H, m), 2.65(4H, brs), 3.55(4H, brs), 4.00 (1H, m), 7.33–7.49(2H, m), 7.80(1H, d, J=8Hz), 7.90 (1H, d, J=8Hz). |
| 54 | 158 | | 0.95(1H, m), 1.3–1.9(15H, m), 2.10(1H, m), 2.20(2H, brs), 2.45(4H, brs), 2.80 (2H, m), 3.80(4H, brs), 4.00 (1H, m), 6.48(1H, t, J=4.6Hz), 8.35(2H, d, J=4.6Hz). |
| 55 | 159 | 92 | |
| 56 | 160 | 107 | |
| 57 | 161 | 190–192 | |
| 58 | 162 | 238 | |
| 59 | 163 | 252 | |
| 60 | 164 | 141–143 | 1.4–2.1(12H, m), 2.30–2.51 (4H, m), 2.62(4H, t, J=5Hz), 2.8–2.9(2H, brs), 3.51– 3.60(6H, m), 7.31–7.48(2H, m), 7.79(1H, d, J=8.3Hz), 7.90(1H, d, J=8.3Hz). |
| 61 | 165 | 212–213 | 1.25–1.95(14H, m), 2.05– 2.35(3H, m), 2.5–2.85(8H, m), 3.55–3.7(4H, m), 3.9– 4.1(1H, m), 7.32–7.49(2H, m), 7.81(1H, d, J=8Hz), 7.93(1H, d, J=8Hz). |
| 62 | 166 | 143–145 | 0.9–2.2(23H, m), 2.5–2.6 (1H, m), 2.6(2H, s), 2.7(2H, s), 2.9–3.1(3H, m), 3.3(1H, dd, J=13 and 10Hz), 4.0(1H, dd, J=13 and 4Hz), 6.85– 6.93(1H, m), 7.07(1H, dd, J= 2 and 9Hz), 7.7(1H, dd, J= 5 and 8Hz), 9.79(1H, brs). |
| 63 | 167 | 215–216 | 1.0–2.2(28H, m), 2.5–2.6 (1H, m), 2.7–3.1(5H, m), 3.34(1H, dd, J=13 and 10Hz), 3.9(1H, dd, J=13 and 4Hz), 6.95(1H, d, J=1Hz), 7.06–7.21(2H, m), 7.36(1H, d, J=8Hz), 7.64(1H, d, J= 8Hz), 7.97(1H, brs). |
| 64 | 168 | 180–181 | 0.9–2.2(24H, m), 2.52–2.58 (1H, m), 2.59(2H, s), 2.7(2H, s), 2.75–2.85(1H, m), 2.9– 3.1(2H, m), 3.31(1H, dd, J= 10 and 13Hz), 3.9(1H, dd, J= 4 and 13Hz), 6.94(1H, d, J= 1Hz), 7.06–7.2(2H, m), 7.34 (1H, d, J=8Hz), 8.0(1H, brs). |
| 65 | 169 | 209–210 | 0.9–2.2(25H, m), 2.5–2.6 (1H, m), 2.8–3.4(6H, m), 3.9–4.0(1H, m), 7.1–7.17 (2H, m), 7.94–7.99(2H, m). |
| 66 | 170 | 129–130 | 0.9–2.2(21H, m), 2.45–2.6 (1H, m), 2.6(2H, s), 2.7(2H, s), 2.9–3.35(4H, m), 3.85– 3.95(1H, m), 7.17–7.17(2H, m), 7.94–7.99(2H, m). |
| 67 | 171 | 186–187 | 1.0–1.4(4H, m), 1.65–1.75 (2H, m), 1.9–2.0(2H, m), 2.5–2.6(2H, m), 2.6–2.8 (8H, m), 3.5–3.65(5H, m), 3.83(1H, d, J=12Hz), 3.8– 3.9(1H, m), 4.62(1H, brs), 4.90(1H, brs), 6.22(1H, dd, J=1.6 and 6Hz), 6.38(1H, dd, J=1.6 and 6Hz), 7.33– |
| 68 | 172 | 124–125 | 7.50(2H, m), 7.81(1H, d, J= 8Hz), 7.91(1H, d, J=8Hz). 1.3–2.0(10H, m), 2.5–2.6 (2H, m), 2.6–2.8(4H, m), 2.8–3.0(2H, m), 3.5–3.7 (5H, m), 3.86(1H, d, J=14Hz), 4.63(1H, brs), 4.9(1H, brs), 6.22(1H, dd, J=1.7 and 6Hz), 6.38(1H, brd, J= 6Hz), 7.33–7.50(2H, m), 7.82(1H, d, J=8Hz), 7.92 (1H, d, J=8Hz). |
| 69 | 173 | 119–120 | 1.1–1.75(6H, m), 1.8–2.2 (6H, m), 2.3–2.8(10H, m), 3.4–3.65(6H, m), 5.6–5.7 (2H, m), 7.33–7.49(2H, m), 7.81(1H, d, J=8Hz), 7.92 (1H, d, J=8Hz). |
| 70 | 174 | 89–90 | 1.35–2.25(14H, m), 2.3–2.9 (8H, m), 3.4–3.7(6H, m), 5.5–5.7(2H, m), 7.33–7.49 (2H, m), 7.81(1H, d, J=8Hz), 7.92(1H, d, J=8Hz). |
| 71 | 175 | 149–151 | 1.2–1.9(16H, m), 2.2–2.45 (4H, m), 2.55–2.7(4H, m), 2.8–2.9(2H, m), 3.5–3.8 (6H, m), 7.32–7.49(2H, m), 7.80(1H, d, J=8Hz), 7.91 (1H, d, J=8Hz). |
| 72 | 176 | 189–191 | 1.1–1.9(4H, m), 2.2–2.7 (12H, m), 3.5–3.8(6H, m), 7.33–7.49(2H, m), 7.8(1H, d, J=8Hz), 7.91(1H, d, J=8Hz). |

What is claimed is:

1. An imide compound of the formula:

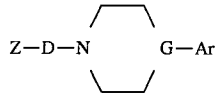

wherein Z is a group of the formula:

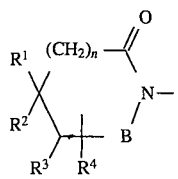

in which B is a carbonyl group or a sulfonyl group, $R^1$, $R^2$, $R^3$ and $R^4$ are each a hydrogen atom or an alkyl group having 1–4 carbon atoms with a proviso that $R^1$ and $R^2$ or $R^1$ and $R^3$ are combined together to make a non-aromatic hydrocarbon ring having at most 7 carbon atoms and being un-substituted or substituted with at least one alkyl group having 1–4 carbon atoms, and n is an integer of 0 or 1;

D is a group of the formula:

$$-(CH_2)_p-A-(CH_2)_q-$$

in which A is a non-aromatic hydrocarbon ring having at most 7 carbon atoms or a non-aromatic hydrocarbon ring having at most 7 carbon atoms which is bridged with an alkylene group having not more than 3 carbon atoms or an oxygen atom, and p and q are each an integer of 0, 1 or 2;

Ar is a benzisothiazolyl group being unsubstituted or substituted with at least one of an alkyl group having 1–4 carbon atoms, an alkoxy group having 1–4 carbon atoms and a halogen atom; and G is >N—; or an acid addition salt thereof.

2. The imide compound according to claim 1, wherein said non-aromatic hydrocarbon ring in Z is further bridged with an alkylene group having 1–3 carbon atoms and being un-substituted or substituted with at least one alkyl group having 1–4 carbon atoms, or an oxygen atom; or an acid addition salt thereof.

3. The imide compound according to claim 1, wherein said non-aromatic hydrocarbon ring in D is further bridged with an alkylene group having 1–3 carbon atoms and being unsubstituted or substituted with at least one alkyl group having 1–4 carbon atoms, or an oxygen atom; or an acid addition salt thereof.

4. The imide compound according to claim 1, wherein said non-aromatic hydrocarbon rings in Z and D are further bridged with an alkylene group having 1–3 carbon atoms and being unsubstituted or substituted with at least one alkyl group having 1–4 carbon atoms, or an oxygen atom; or an acid addition salt thereof.

5. The imide compound according to claim 1, wherein Z is one of the following formulas:

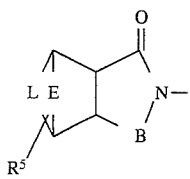
(Z-1)

wherein L is —CH$_2$—CH$_2$— or —CH=CH—, E is an alkylene group having not more than 3 carbon atoms and being un-substituted or substituted with an alkyl group having not more than 4 carbon atoms or an oxygen atom, R$^5$ is a hydrogen atom or an alkyl group having not more than 4 carbon atoms and B is a carbonyl group or a sulfonyl group;

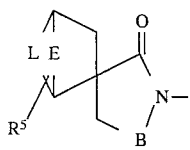
(Z-2)

wherein L, E, R$^5$ and B are each as defined above;

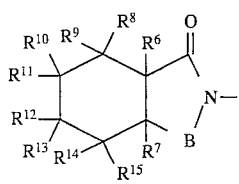
(Z-3)

wherein R$^6$, R$^7$, R$^8$, R$^9$, R$^{10}$, R$^{11}$, R$^{12}$, R$^{13}$, R$^{14}$ and R$^{15}$ are each a hydrogen atom or an alkyl group having not more than 4 carbon atoms, or two of those present at the neighboring positions each other may be combined together to make a bond and B is as defined above; and

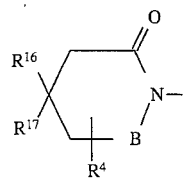
(Z-4)

wherein R$^4$ is a hydrogen atom or an alkyl group having not more than 4 carbon atoms, R$^{16}$ and R$^{17}$ are combined together to make a saturated hydrocarbon ring having not more than 7 carbon atoms, and B is as defined above; or an acid addition salt thereof.

6. An imide compound of the formula:

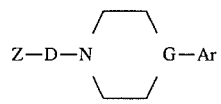

wherein

Z is a group of the formula:

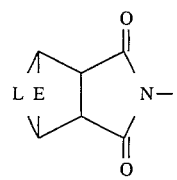

wherein L is —CH$_2$—CH$_2$— or —CH=CH—, E is an alkylene group having not more than 3 carbon atoms;

D is a group of the formula:

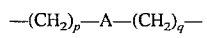
—(CH$_2$)$_p$—A—(CH$_2$)$_q$— wherein A is a cycloalkane ring having not more than 7 carbon atoms or a cycloalkane ring having not more than 7 carbon atoms which is bridged with an alkylene group having not more than 3 carbon atoms, or an oxygen atom, p and q are each an integer of 0, 1 or 2;

Ar is a benzisothiazolyl group; and

G is >N— or an acid addition salt thereof.

7. The imide compound according to claim 7, wherein said cycloalkane ring in D is further bridged with an alkylene group having 1–3 carbon atoms; or an acid addition salt thereof.

8. The imide compound according to claim 7 or 8, wherein Z is a group of the formula:

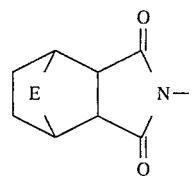

wherein E is a methylene group or an ethylene group; or an acid addition salt thereof.

9. The imide compound according to claim 7 or 8, wherein D is a group of the formula:

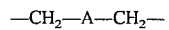
—CH$_2$—A—CH$_2$— wherein A is as defined above; or an acid addition salt thereof.

10. The imide compound according to claim 10, wherein A is a cyclohexane ring; or an acid addition salt thereof.

11. The imide compound of the formula:

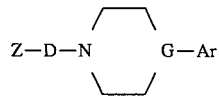

wherein
Z is a group of the formula:

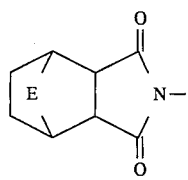

wherein E is a methylene group or an ethylene group;
D is a group of the formula:

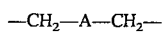

wherein A is a cycloalkane ring having not more than 7 carbon atoms or a cycloalkane ring having not more than 7 carbon atoms which is bridged with an alkylene group having not more than 3 carbon atoms, or an oxygen atom;
Ar is a benzisothiazolyl group; and
G is >N—; or an acid addition salt thereof.

12. The imide compound according to claim 14, wherein E is a methylene group; or an acid addition salt thereof.

13. The imide compound according to claim 14 or 15, wherein A is a 1,2-cyclohexane-diyl group; or an acid addition salt thereof.

14. The imide compound of the formula:

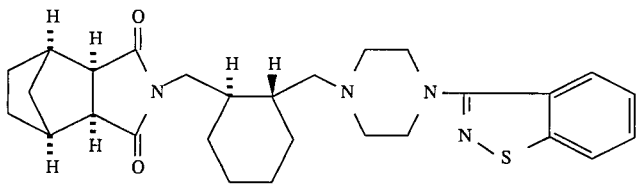

or an acid addition salt thereof.

15. The imide compound of the formula:

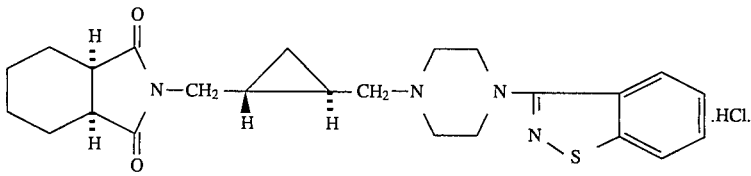

16. The imide compound of one of the following formulae:

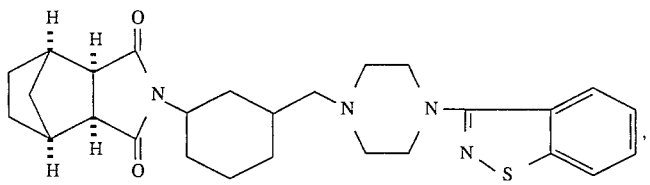

17. The imide compound of the formula:

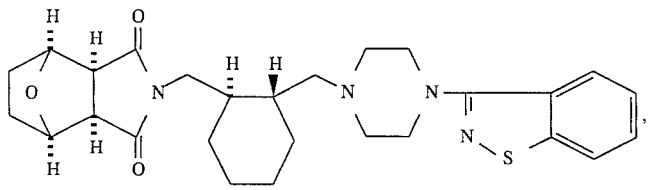

or an acid addition salt thereof.

18. The imide compound of the formula:

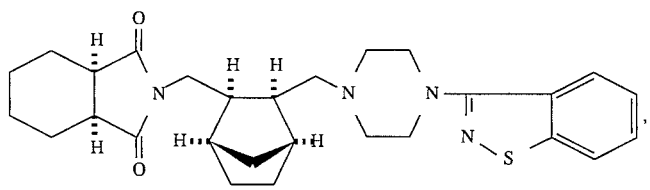

or an acid additional salt thereof.

19. The imide compound of the formula:

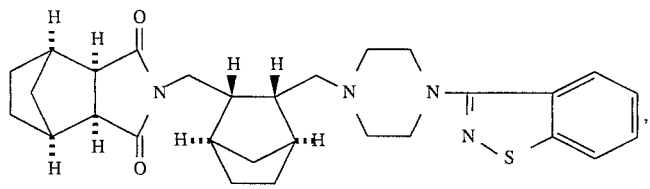

or an acid addition salt thereof.

20. The imide compound according to claim 1, wherein said non-aromatic hydrocarbon ring and said alkylene group in the definition of A are each substituted with at least one alkyl group having 1–4 carbon atoms.

* * * * *

UNITED STATES PATENT AND TRADEMARK OFFICE
CERTIFICATE OF CORRECTION

PATENT NO.         : 5,532,372
APPLICATION NO. : 08/113320
DATED                 : July 2, 1996
INVENTOR(S)       : Ikutaro Saji et al.

It is certified that error appears in the above-identified patent and that said Letters Patent is hereby corrected as shown below:

Col. 62 Line 45-49 in Claim 7, the line reading "The imide compound according to claim 7, wherein" should read --The imide compound according to claim 6, wherein--.

Col. 62 Line 49-50 in Claim 8, the line reading "The imide compound according to claim 7 or 8," should read --The imide compound according to claim 6 or 7,--.

Col. 62 Line 61-62 in Claim 9, the line reading "The imide compound according to claim 7 or 8," should read --The imide compound according to claim 6 or 7,--.

Col. 63 Line 1-2 in Claim 10, the line reading "The imide compound according to claim 10, wherein" should read --The imide compound according to claim 9, wherein--.

UNITED STATES PATENT AND TRADEMARK OFFICE
CERTIFICATE OF CORRECTION

PATENT NO. : 5,532,372
APPLICATION NO. : 08/113320
DATED : July 2, 1996
INVENTOR(S) : Ikutaro Saji et al.

It is certified that error appears in the above-identified patent and that said Letters Patent is hereby corrected as shown below:

Col. 63 Line 31-32 in Claim 12, the line reading "The imide compound according to claim 14, wherein" should read --The imide compound according to claim 11, wherein--.

Col. 63 Line 34-35 in Claim 13, the line reading "The imide compound according to claim 14 or 15," should read --The imide compound according to claim 11 or 12,--.

Signed and Sealed this

Twenty-fourth Day of November, 2009

David J. Kappos
*Director of the United States Patent and Trademark Office*